(12) United States Patent
Bentley et al.

(10) Patent No.: US 12,329,574 B2
(45) Date of Patent: Jun. 17, 2025

(54) FIDUCIAL SYSTEMS FOR PROBE TRACKING AND IDENTIFICATION

(71) Applicant: PROCEPT BioRobotics Corporation, Redwood City, CA (US)

(72) Inventors: Peter Bentley, Reno, NV (US); Nishey Wanchoo, San Mateo, CA (US); Qingxiang Ke, San Jose, CA (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 278 days.

(21) Appl. No.: 18/051,414

(22) Filed: Oct. 31, 2022

(65) Prior Publication Data

US 2024/0138808 A1    May 2, 2024

(51) Int. Cl.
*A61B 8/00* (2006.01)
*A61B 8/12* (2006.01)
*A61B 90/00* (2016.01)

(52) U.S. Cl.
CPC .............. *A61B 8/4254* (2013.01); *A61B 8/12* (2013.01); *A61B 8/4422* (2013.01); *A61B 90/39* (2016.02); *A61B 2090/3945* (2016.02)

(58) Field of Classification Search
CPC .................................................. A61B 8/4254
See application file for complete search history.

(56) References Cited

U.S. PATENT DOCUMENTS

| 8,152,816 | B2 | 4/2012 | Tuma |
| 8,229,188 | B2 | 7/2012 | Rusko |
| 9,144,461 | B2 | 9/2015 | Kruecker |
| 9,277,969 | B2 | 3/2016 | Brannan |
| 10,226,298 | B2 | 3/2019 | Ourselin |
| 10,423,757 | B2 | 9/2019 | Kruecker |
| 10,448,956 | B2 | 10/2019 | Gordon |
| 11,278,451 | B2 | 3/2022 | Andrews |
| 2008/0027420 | A1 | 1/2008 | Wang |
| 2011/0299750 | A1 | 12/2011 | Cool |

(Continued)

FOREIGN PATENT DOCUMENTS

| CN | 113633372 | 11/2021 |
| CN | 113796952 | 12/2021 |

(Continued)

OTHER PUBLICATIONS

Co-pending U.S. Appl. No. 18/163,187, filed Feb. 1, 2023.

(Continued)

*Primary Examiner* — Joseph M Santos Rodriguez
(74) *Attorney, Agent, or Firm* — FisherBroyles, LLP; John K. Shimmick

(57) ABSTRACT

A system for determining a position or an orientation of a probe across a drape may include a fiducial assembly that may be coupled to the probe though a drape. The fiducial assembly may include a base, a coupling attached to the base which may be configured to couple the fiducial assembly to the probe across the drape, and one or more fiducials attached to the base. Coupling the fiducials to the probe across the drape can allow sterile fiducials to be coupled to a non-sterile probe to determine the position and orientation of the probe based on images from the of the fiducials on a sterile side of the drape. In some embodiments, the fiducial is aligned with respect to an elongate axis of the probe with a predetermined offset and orientation with respect to the elongate axis of the probe.

19 Claims, 13 Drawing Sheets

(56) References Cited

U.S. PATENT DOCUMENTS

| | | | |
|---|---|---|---|
| 2012/0130241 A1 | 5/2012 | Wang |
| 2016/0256225 A1 | 9/2016 | Crawford |
| 2016/0332005 A1 | 11/2016 | Fedewa |
| 2017/0273797 A1 | 9/2017 | Gordon |
| 2017/0333137 A1 | 11/2017 | Roessler |
| 2018/0028261 A1 | 2/2018 | Chen |
| 2018/0318011 A1 | 11/2018 | Leibinger |
| 2019/0000319 A1 | 1/2019 | Mak |
| 2019/0064290 A1 | 2/2019 | Bailey |
| 2019/0069962 A1 | 3/2019 | Tabandeh |
| 2019/0201214 A1 | 7/2019 | Miller |
| 2020/0360100 A1 | 11/2020 | Mantri |
| 2020/0375622 A1 | 12/2020 | Aljuri |
| 2021/0121251 A1 | 4/2021 | Aljuri |
| 2022/0133331 A1 | 5/2022 | Abbasi |
| 2022/0241037 A1 | 8/2022 | Crawford |
| 2022/0241981 A1 | 8/2022 | Fredrickson |
| 2024/0285346 A1 | 8/2024 | Shi |
| 2024/0299003 A1 | 9/2024 | Shi |

FOREIGN PATENT DOCUMENTS

| | | |
|---|---|---|
| CN | 113940753 | 1/2022 |
| CN | 113951935 | 1/2022 |
| CN | 114145781 | 3/2022 |
| CN | 114320879 | 4/2022 |
| CN | 114376610 | 4/2022 |
| CN | 114521939 | 5/2022 |
| CN | 216495529 | 5/2022 |
| CN | 216675776 | 6/2022 |
| CN | 216675785 | 6/2022 |
| CN | 217338655 | 9/2022 |
| EP | 1486900 | 12/2004 |
| KR | 101869826 | 6/2018 |
| WO | 2008083407 | 7/2008 |
| WO | 2009111736 | 9/2009 |
| WO | 2011097505 | 8/2011 |
| WO | 2013053614 | 4/2013 |
| WO | 2013130895 | 9/2013 |
| WO | 2014127242 | 8/2014 |
| WO | 2014165703 | 10/2014 |
| WO | 2015035249 | 3/2015 |
| WO | 2015200538 | 12/2015 |
| WO | 2016004071 | 1/2016 |
| WO | 2016037132 | 3/2016 |
| WO | 2016037137 | 3/2016 |
| WO | 2017161331 | 9/2017 |
| WO | 2019032986 | 2/2019 |
| WO | 2019137665 | 7/2019 |
| WO | 2019246580 | 12/2019 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |
| WO | 2021096741 | 5/2021 |
| WO | 2021262565 | 12/2021 |
| WO | 2021263276 | 12/2021 |
| WO | 2022006248 | 1/2022 |
| WO | 2022011177 | 1/2022 |
| WO | 2022226103 | 10/2022 |
| WO | 2023066148 | 4/2023 |
| WO | 2023072146 | 5/2023 |
| WO | 2023083352 | 5/2023 |
| WO | 2023088305 | 5/2023 |
| WO | 2023159096 | 8/2023 |
| WO | 2023159101 | 8/2023 |
| WO | 2023179756 | 9/2023 |
| WO | 2023207917 | 11/2023 |

OTHER PUBLICATIONS

International Search Report and Written Opinion for PCT/US2023/77776, 14 pages (Apr. 30, 2024).

Garnica-Garza, HM. Directional scatter imaging for the stereoscopic tracking of fiducial markers in a single kV exposure. Med Phys. Feb. 2018;45(2):703-713. doi: 10.1002/mp.12712. Epub Dec. 21, 2017. PMID: 29206280.

Koák M, Slabý A. Designing a Simple Fiducial Marker for Localization in Spatial Scenes Using Neural Networks. Sensors (Basel). Aug. 10, 2021;21(16):5407. doi: 10.3390/s21165407. PMID: 34450848; PMCID: PMC8400176.

Stathakis, Alexandros, "Vision-Based Localization using Reliable Fiducial Markers," retrieved from https://citeseerx.ist.psu.edu/viewdoc/download?doi=10.1.1.895.3616&rep=rep1&type=pdf (Dec. 2011).

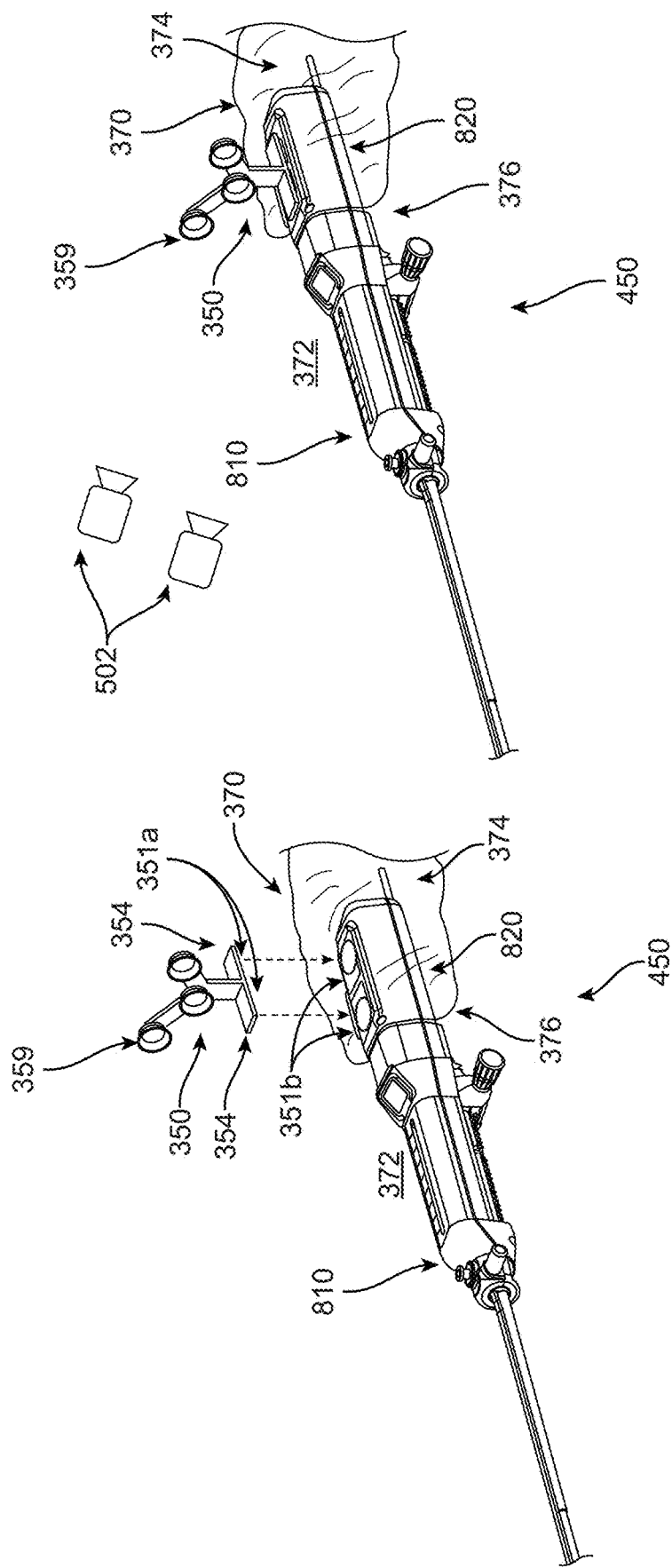

FIDUCIAL SYSTEMS FOR PROBE TRACKING AND IDENTIFICATION

CROSS REFERENCE

None

BACKGROUND

Prior approaches to locating and aligning surgical probes can be less than ideal in at least some respects. Work in relation to the present disclosure suggests that misalignment of surgical probes in the prior approaches can result in cutting and treating tissue with less accuracy and can be somewhat more invasive than would be ideal in at least some instances. At least some of the prior approaches may align an imaging element and a treatment probe with less accuracy than would be ideal, which can lead to less than ideal tissue treatment. Although robotics approaches can provide alignment with computer control, at least some of the prior robotics systems may not align a probe inserted into a patent with the anatomy of the as accurately as would be ideal. Although treatments with fiducials have been proposed, the prior approaches may provide less than ideal coordination and positioning of imaging probes and surgical probes in at least some instances. In some prior approaches, surgical drapes may potentially interfere with the use of fiducials in at least some instances.

SUMMARY

The presently disclosed probes, systems and methods are related to improved alignment of probes and in some embodiments the alignment of imaging probes with treatment probes and associated of energy sources. The presently disclosed fiducial assembly may comprise a coupling configured to couple to a probe across a drape in order to maintain a sterile surgical field when the coupling is connected to the probe and the fiducial is used to determine one or more of a position or an orientation of the probe. In some embodiments, the fiducial is used to determine the position and orientation in the probe, which may comprise a 6 degree of freedom pose of the probe. In some embodiments, a fiducial system comprises a fiducial assembly that may be coupled to a probe though a drape such as a sterile surgical drape. In some embodiments, the fiducial assembly is aligned with respect to an elongate axis of the probe with a predetermined offset and orientation with respect to the elongate axis of the probe. The fiducial assembly may include a base, a coupling attached to the base, in which the coupling is configured to couple the fiducial assembly to the probe across the surgical drape, and one or more fiducials attached to the base. In some embodiments, the fiducial is aligned with respect to an elongate axis of the probe with a predetermined offset and orientation with respect to the elongate axis of the probe. The offset can be configured in many ways and may comprise one or more of an angular offset, a radial offset, a longitudinal offset, or a pitch offset or a yaw offset with respect to an axis of the probe. In some embodiments, the fiducial is coupled to the probe with a predetermined longitudinal offset from a distal tip of the probe, such that the position and orientation of the fiducial can be used to determine the position and orientation of the distal tip of the probe. Coupling the fiducial to the probe across the drape can allow sterile fiducials to be coupled to a non-sterile probe, or a non-sterile instrument driver, in order to determine the position and orientation of the probe across the drape based on images of the fiducials on a sterile side of the drape, while maintaining a sterile surgical field.

In some embodiments, a system may include a sterile probe configured to be located on a sterile side of a surgical drape, and a non-sterile instrument driver configured to couple to the probe. In some embodiments, the instrument driver is located on a non-sterile side of the drape, and the sterile probe and the instrument driver are configured to couple to each other across the surgical drape. In some embodiments, the system may include a one or more sterile fiducials in a fixed spatial relationship with a sterile portion of the probe. In some embodiments, the one or more sterile fiducials are attached to the sterile probe. Alternatively or in combination, the one of more fiducials can be connected to a non-sterile instrument driver across the drape, in which the position and orientation of the probe is determined in response to the position and orientation of the fiducials on the instrument driver.

In some embodiments, a method of using fiducials with a drape comprises coupling a probe comprising an elongate shaft and an elongate axis to an arm, covering the probe with a drape and coupling a fiducial assembly to the probe though the drape with the drape between the fiducial assembly and the probe. While the fiducial assembly can be configured in many ways, in some embodiments the fiducial assembly comprises a base, a coupling attached to the base and configured to couple the fiducial assembly to the probe across the drape, and one or more fiducials attached to the base.

In some embodiments, a method of using a drape comprises covering a non-sterile instrument driver with a drape, and coupling a sterile probe to the instrument driver, with the surgical drape therebetween, wherein one or more sterile fiducials is coupled to the sterile probe in a fixed special relationship with the sterile portion of the surgical probe.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 9A shows a surgical probe with couplable fiducials, in accordance with some embodiments of the present disclosure;

FIG. 9B shows a surgical probe with couplable fiducials, in accordance with some embodiments of the present disclosure;

DETAILED DESCRIPTION

Figure 1:
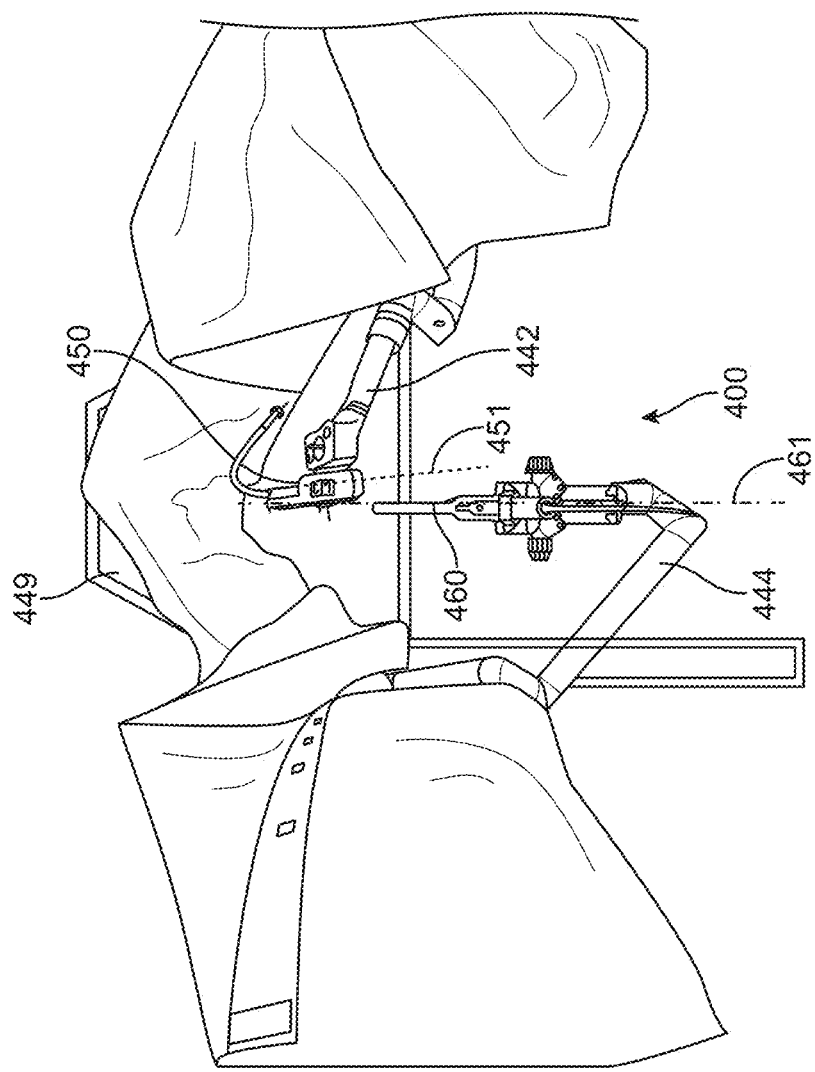
FIG. 1 shows a front view of a system for performing tissue resection in a patient, in accordance with some embodiments of the present disclosure.

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed systems and methods are well suited for use with many probes and diagnostic and surgical procedures. Although reference is made to a treatment probe comprising an energy source for prostate surgery and a transrectal ultrasound ("TRUS") probe, the present disclosure is well suited for use with many types of probes inserted into many types of tissues, organs, cavities and lumens, such as brain, heart, lung, intestinal, eye, skin, kidney, liver, pancreas, stomach, uterus, ovaries, testicles, bladder, ear, nose, mouth, tumors, cancers, soft tissues such as bone marrow, adipose tissue, muscle, glandular and mucosal tissue, spinal and nerve tissue, cartilage, hard biological tissues such as teeth, bone, and lumens such as vascular lumens, nasal lumens and cavities, sinuses, colon, urethral lumens, gastric lumens, airways, esophageal lumens, trans esophageal, intestinal lumens, anal lumens, vaginal lumens, trans abdominal, abdominal cavities, throat, airways, lung passages, and surgery such as kidney surgery, ureter surgery, kidney stones, prostate surgery, tumor surgery, cancer surgery, brain surgery, heart surgery, eye surgery, conjunctival surgery, liver surgery, gall bladder surgery, bladder surgery, spinal surgery, orthopedic surgery, arthroscopic surgery, liposuction, colonoscopy, intubation, minimally invasive incisions, minimally invasive surgery, and others.

The presently disclosed systems and methods are well suited for combination with prior probes such as imaging probes and treatment probes. Examples of such probes include laser treatment probes, water jet probes, RF treatment probes, radiation therapy probes, ultrasound treatment probes, phaco emulsification probes, imaging probes, endoscopic probes, resectoscope probes, ultrasound imaging probes, A-scan ultrasound probes, B-scan ultrasound probes, 3D ultrasound probes, Doppler ultrasound probes, transrectal ultrasound probes, transvaginal ultrasound probes, sagittal plane ultrasound imaging probes, transverse plane ultrasound imaging probes, and transverse and sagittal plane ultrasound imaging probes, for example.

The presently disclosed systems, methods and apparatuses are well suited for combination with many prior surgical procedures, such as water jet enucleation of the prostate, transurethral resection of the prostate (TURP), holmium laser enucleation of the prostate (HOLEP), prostate brachytherapy and with surgical robotics systems and automated surgical procedures. The following patent applications describe examples of systems, methods, probes and procedures suitable for incorporation in accordance with the present disclosure: PCT/US2013/028441, filed Feb. 28, 2013, entitled "AUTOMATED IMAGE-GUIDED TISSUE RESECTION AND TREATMENT, published as WO 2013/130895; PCT/US2014/054412, filed Sep. 5, 2014, entitled "AUTOMATED IMAGE-GUIDED TISSUE RESECTION AND TREATMENT", published as WO 2015/035249; PCT/US2015/048695, filed Sep. 5, 2015, entitled "PHYSICIAN CONTROLLED TISSUE RESECTION INTEGRATED WITH TREATMENT MAPPING OF TARGET ORGAN IMAGES", published as WO2016037137; PCT/US2019/038574, filed Jun. 21, 2019, entitled "ARTIFICIAL INTELLIGENCE FOR ROBOTIC SURGERY", published as WO2019246580A1 on Dec. 26, 2019; PCT/US2020/021756, filed Mar. 9, 2020, entitled "ROBOTIC ARMS AND METHODS FOR TISSUE RESECTION AND IMAGING", published as WO/2020/181290; PCT/US2020/058884, filed on Nov. 4, 2020, entitled "SURGICAL PROBES FOR TISSUE RESECTION WITH ROBOTIC ARMS", published as WO/2021/096741; PCT/US2021/070760, filed on Jun. 23, 2021, entitled "INTEGRATION OF ROBOTIC ARMS WITH SURGICAL PROBES", published as WO/2021/263276; and PCT/US2021/038175, filed on Jun. 21, 2021, entitled "SYSTEMS AND METHODS FOR DEFINING AND MODIFYING RANGE OF MOTION OF PROBE USED IN PATIENT TREATMENT", published as WO/2021/262565; the entire disclosures of which are incorporated herein by reference.

In some embodiments, improved positional accuracy is provided for placement of an energy source and imaging probe. The energy source may comprise any suitable energy source, such as an electrode, a loop electrode, laser source, mechanical sheer, ultrasound probe, cavitating ultrasound probe, a water jet, e.g. a fixed pressure water jet, plasma, steam, a morcellator, a trans urethral needle, photo ablation, water jet evacuation. The energy source can be combined with other treatments and compounds, such as photochemical treatment agents. The imaging probe may comprise any suitable probe, such as endoscopic probes, resectoscope probes, ultrasound imaging probes, A-scan ultrasound probes, B-scan ultrasound probes, Doppler ultrasound probes, transrectal ultrasound probes, transvaginal ultrasound probes, sagittal plane ultrasound imaging probes, transverse plane ultrasound imaging probes, and transverse and sagittal plane ultrasound imaging probes, for example.

The probes comprising the energy source and the imaging probes can be configured in many ways and each may comprise one or more fiducials for determining a position and orientation of a respective probe.

FIG. 1 shows an exemplary embodiment of a system 400 for performing treatment of a patient. The system 400 may comprise a treatment probe 450 as described herein and an imaging probe 460 as described herein. The treatment probe 450 may be coupled to a first arm 442, and the imaging probe 460 coupled to a second arm 444. One or both of the first arm 442 and the second arm 444 may comprise robotic arms whose movements may be controlled by one or more computing devices operably coupled with the arms. The treatment probe 450 may comprise a device for removing target tissue from a target site within a patient. The treatment probe 450 may be configured to deliver energy from the treatment probe 450 to the target tissue sufficient for removing the target tissue. For example, the treatment probe 450 may comprise an electrosurgical ablation device, a laser ablation device, a transurethral needle ablation device, a water jet ablation device, a steam ablation device, a high-intensity focused ultrasound (HIFU) device, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms. Further details regarding the various components of the system 400 suitable for incorporation with embodiments as disclosed herein may be found in U.S. Pat. Nos. 7,882,841, 8,814,921, 9,364,251, and PCT Publication No. WO2013/130895, the entire disclosures of which are incorporated herein by reference.

Figure 2:
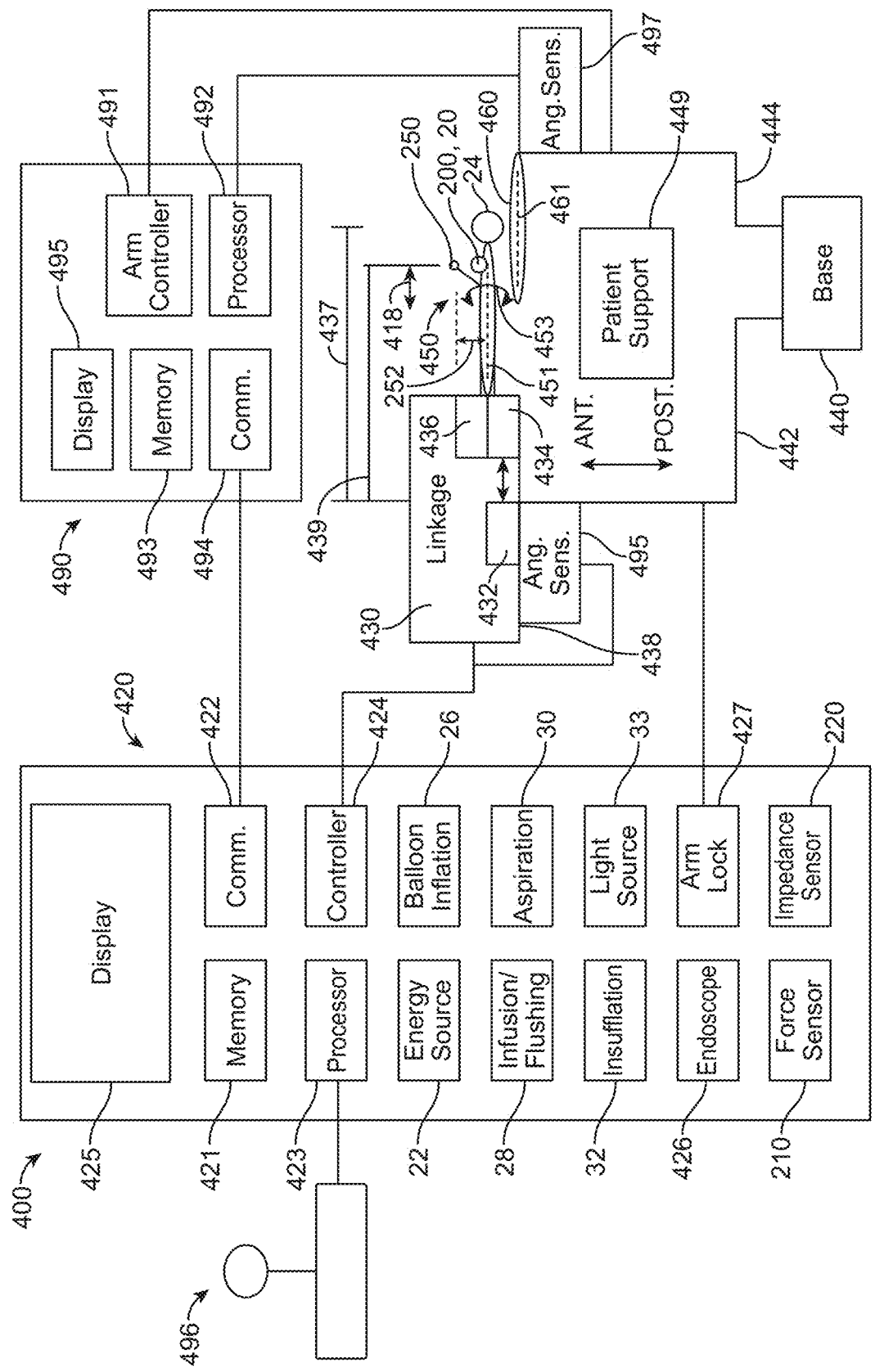
FIG. 2 schematically illustrates a system for performing tissue resection in a patient, in accordance with some embodiments of the present disclosure.

FIG. 2 schematically illustrates embodiments of the system 400 for performing tissue resection in a patient. The system 400 may comprise a treatment probe 450 as described herein and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. A user input device 496 can be located in any suitable place, for example, on a console, on a robotic arm, on a mobile base, and there may be one, two, three, four, or more user input devices used in conjunction with the system 400 to either provide redundant avenues of input, unique input commands, or a combination. In some embodiments, the user input device comprises a controller to move the end of the treatment probe or the imaging probe with movements in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The processor can be configured with instructions for the probe control to switch between automated image guidance treatment with the energy source and treatment with the energy source with user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways.

During insertion, each of the first and second arms may comprise a substantially unlocked configuration such the treatment or imaging probe can be desirably rotated and translated in order to insert the probe into the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 460 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively or in combination, the second angle sensor 497 may be coupled to the controller 424 of the treatment console 420.

The console 420 comprises a display 425 coupled to a processor system in components that are used to control treatment probe 450. The console 420 comprises a processor 423 having a memory 421. Communication circuitry 422 is coupled to processor 423 and controller 424. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

In some embodiments, the console 420 comprises impedance sensor circuitry 220 coupled to the energy source to measure impedance of tissue treated with energy from the energy source. In some embodiments, the energy source comprises an electrode and the electrode comprises an impedance sensor. In some embodiments, the processor is configured with instructions to adjust an amount of energy from the energy source in response to an amount of impedance. In some embodiments, the processor is configured with instructions to adjust an amount of deflection of the extension and offset of the energy source from the elongate axis in response to impedance.

In some embodiments, the console 420 comprises force sensor circuitry 210 coupled to a force sensor on the treatment probe. The force sensor can be coupled to the extension to measure tissue resistance related to deflection of the extension, for example. In some embodiments, the force sensor is coupled to the link to measure tissue resistance related to movement of the energy source away from the elongate axis. In some embodiments, the force sensor is coupled to the energy source to measure tissue resistance related to a positioning distance of the energy source from the elongate axis. In some embodiments, the force sensor is configured to measure tissue resistance related to an amount of energy delivery from the energy source.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 32 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450. In some embodiments, the probe comprises a first energy source 250 that can be offset from the elongate axis 451 the probe with an offset 252 a distance to treat tissue, for example with deflection of an extension as described herein. The processor can be configured with instructions to perform 3D volumetric resection of the tissue with rotation, translation and offset of the energy source 250 in response to computer control. The probe 450 may comprise a second energy source as described herein such as a nozzle 200.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed at a substantially constant distance 437 to the anchor 24. The substantially fixed distance 437 between the anchor 24 and the fixed first portion 432 of the linkage allows the treatment to be accurately placed. The first portion 432 may comprise a linear actuator to accurately position the second energy source such as high-pressure nozzle 200 in the energy delivery region 20 at a desired axial position along an elongate axis 451 of treatment probe 450. Additional actuators and linkages can be provided and operatively coupled to the processor to offset, rotate, and translate the first energy source 250 as described herein.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust with translation 418 of the probe in response to computer control to set a target location along the elongate axis 451 of the treatment probe. In some embodiments, the first portion of the linkage remains fixed, while the second portion 434 adjusts the position of the energy delivery region 20 along the axis 451. The third portion 436 of the linkage adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 425.

In order to facilitate precise control of the treatment probe and/or the imaging probe during treatment of the patient, one or more the treatment probe or the imaging probe may be coupled to a robotic, computer-controllable arm. For example, referring to system 400 shown in FIG. 2, one or both of the first arm 442 coupled to the treatment probe 450 as described herein and the second arm 444 coupled to the imaging probe 460 may comprise robotic, computer-controllable arms. The robotic arms may be operably coupled with one or more computing devices configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

The robotic arm may comprise 6 or 7 or more joints to allow the arm to move under computer control. Suitable robotic arms are commercially available from several manufacturers such as RoboDK Inc., Kinova Inc. and several other manufacturers.

The one or more computing devices operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters. The robotic arms may be configured to automatically move the treatment probe and/or imaging probe along a pre-planned or programmed treatment or scanning profile, which may be stored on a memory of the one or more computing devices. Alternatively or additionally to automatic adjustment of the robotic arms, the one or more computing devices may be configured to control movement of the treatment probe and/or the imaging probe in response to user inputs, for example through a graphical user interface of the treatment apparatus. Alternatively or additionally to automatic adjustment of the robotic arms, the one or more computing devices may be configured to control movement of the treatment probe and/or the imaging probe in response to real-time positioning information, for example in response to anatomy recognized in one or more images captured by the imaging probe or other imaging source (from which allowable ranges of motion of the treatment probe and/or the imaging probe may be established) and/or position information of the treatment probe and/or imaging probe from one or more sensors coupled to the probes and/or robotic arms.

Figure 3C:
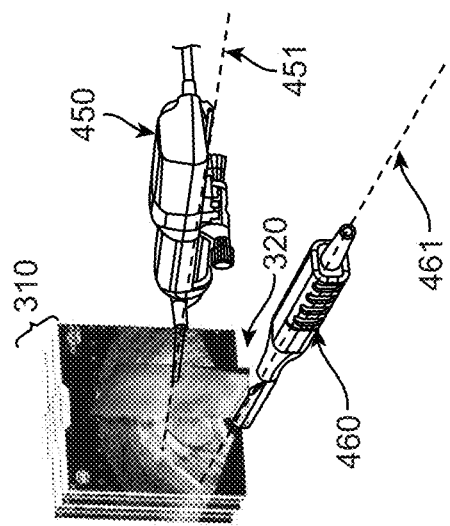
FIG. 3C shows a perspective view of an arrangement of probes, in accordance with some embodiments of the present disclosure.
Figure 3B:
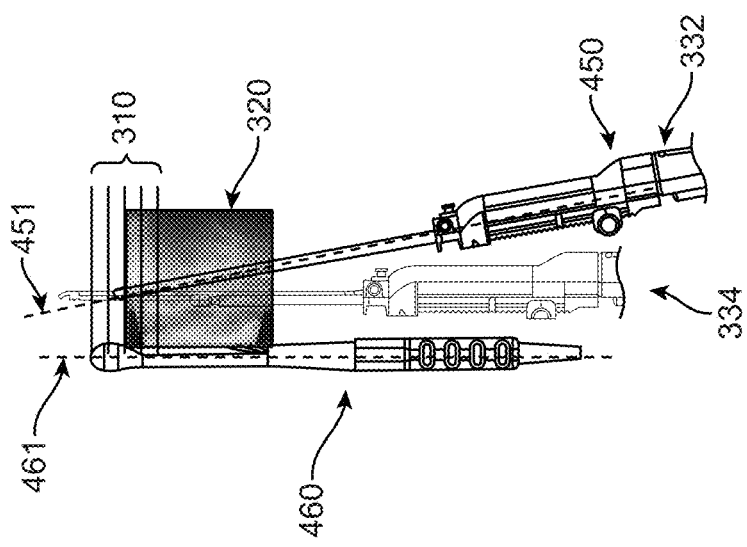
FIG. 3B shows a sagittal view of an arrangement of probes, in accordance with some embodiments of the present disclosure.
Figure 3A:
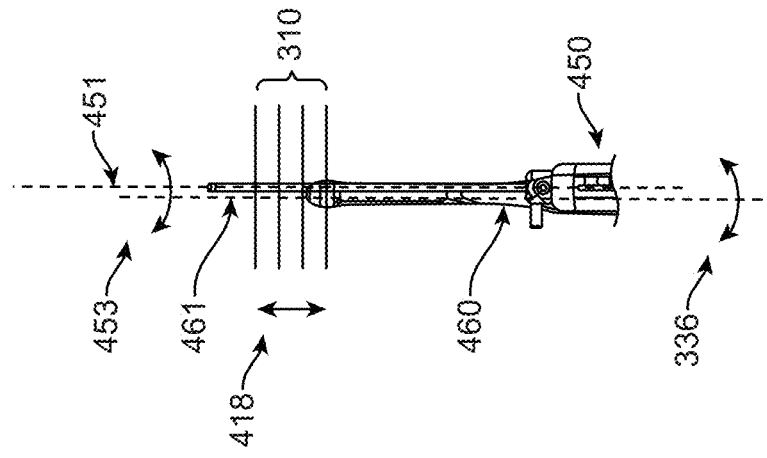
FIG. 3A shows a superior view of an arrangement of probes, in accordance with some embodiments of the present disclosure.

FIGS. 3A, 3B, and 3C show superior, sagittal, and perspective views, respectively, of an arrangement of probes for use in treatment of tissue. In particular, FIGS. 3A, 3B, and 3C show the relative arrangement, including position and orientation of a treatment probe 450 with respect to the position and orientation of an imaging probe 460 for the treatment of tissue such as prostate tissue. The imaging probe 460 can be configured to generate transverse images such as transverse ultrasound images 310 and one or more sagittal images such as one or more sagittal ultrasound images 320. In some embodiments, the energy source of treatment probe 450 is moved with rotation angle 453 and translation 418, such that the treated tissue and the energy source are within the field of view of the imaging probe 460.

As shown in the superior view of FIG. 3A, the treatment probe axis 451 and the imaging probe axis 461 are positioned in a substantially coplanar configuration, such that the imaging probe and the treatment probe extend along a common plane. As shown in the superior view of FIG. 3B and the perspective view of FIG. 3C, the treatment probe axis 451 and the imaging probe axis 461 are positioned in a substantially coplanar and non-parallel configuration, such that the imaging probe and the treatment probe substantially extend along a common plane, which allows the imaging probe to image the treatment probe along the length of translation 418 with sagittal images such as real time sagittal images. In some embodiments, the treatment probe and the imaging probe are arranged in a substantially coplanar configuration, and the ultrasound probe is rotated to rotate the sagittal field of view of the imaging probe in order to image the treatment probe along a length of the sagittal field of view. Referring again to FIG. 3A, the imaging probe 460 can be rotated about elongate axis 461 by an angle 336 to align the treatment probe 450 so as to be within the sagittal field of view, such that the sagittal field of view of the imaging probe is aligned with elongate axis 451 of the treatment probe, for example.

One or more of the treatment probe or the imaging probe can be moved to adjust alignment between the imaging probe and the treatment probe. In some embodiments, the proximal portion of treatment probe is moved from a first position to a second position. Referring again to FIG. 3B, the treatment probe 450 can be moved from a first position 332 to a second position 334 to adjust alignment between the probes, for example based on data from one or more fiducials as described herein.

In some embodiments, the imaging probe 460 and the treatment probe 450 are aligned to be substantially coplanar with each other within a margin of error so that the imaging probe 460 can image the treatment probe 450 and the treatment probe's energy source during treatment, for example with the treatment probe located within a field of view of the imaging probe such as a sagittal image field of view. In some embodiments, the treatment probe is aligned with the imaging probe, such that the treatment probe is visible along a length of a sagittal view of the imaging probe.

In some embodiments, the imaging probe 460 and the treatment probe 450 may be somewhat misaligned, e.g. by more than the margin of error, such that the treatment probe may disappear from a portion of the sagittal image because part of the imaging probe extends beyond the sagittal field of view, for example. In some embodiments, this may result in the imaging probe 460 not imaging a portion of the treatment with sagittal images. In some embodiments, the treatment probe 450 and the imaging probe 460 may be arranged in a substantially skewed orientation as described herein, e.g. outside the margin of error, such that the treatment probe extends outside the sagittal field of view of the imaging probe but is located within the field of view of transverse images of the imaging probe. In such embodiments, the treatment can be monitored in real time with transverse images, in which the imaging probe moves to maintain the energy source and concurrently treated tissue within the transverse field of view of the imaging probe. In some embodiments, a transverse view of the tissue and energy source can decrease sensitivity to alignment between the two probes, and the imaging probe can be moved with the energy source, for example synchronously, to image the tissue and the energy source during treatment.

Figure 3D:
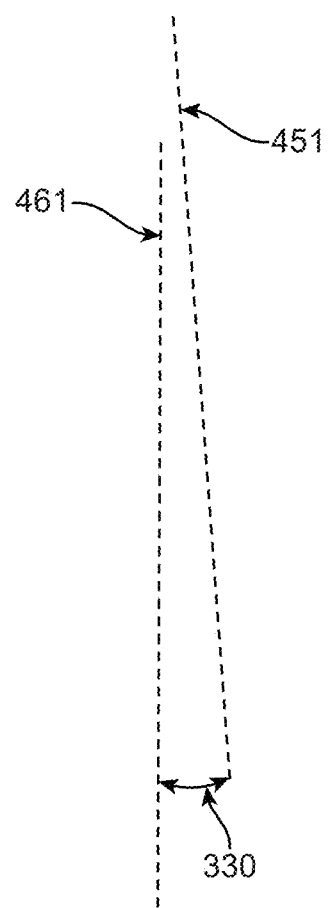
FIG. 3D shows a treatment probe axis and an imaging probe axis skewed with respect to each other by an angle 330, such that the treatment probe and the imaging probe do not extend along a common plane, in accordance with some embodiments of the present disclosure.

FIG. 3D shows the treatment probe axis 451 and the imaging probe axis 461 skewed with respect to each other by an angle 330, such that the treatment probe and the imaging probe do not extend along a common plane. By adjusting the treatment probe or the imaging probe, or both, this skew angle can be decreased. The one or more fiducials as described herein can be used to adjust one or more of the probes to decrease the skew angle between the probes. The amount of acceptable skew may depend on several factors such as the field of view of the imaging probe, the length of tissue treated with the one or more of rotating or translating energy source. In some embodiments, the margin of error of the skew angle is any one of no more than 10 degrees, no more than 5 degrees, no more than 3 degrees, no more than 2 degrees, or no more than 1 degree, for example. In some embodiments, the margin of error of alignment corresponds to a sagittal field of view of the imaging probe and a skew angle between the imaging probe and the treatment probe. When the treatment probe and the imaging probe are aligned within the margin of error, the treatment probe is located within the sagittal field of view along the translation length of the treatment and can be viewed in one or more real-time sagittal images along a length of the sagittal field of view. When the treatment probe and the imaging probe are aligned outside the margin of error, a portion of the treatment probe is located outside the sagittal field of view and may disappear from a portion of an image along a length of the sagittal field of view. In such embodiments, transverse imaging can be used to view the treatment in real time as described herein.

In some embodiments, one or more of the position or the orientation of one or more of the imaging probe 460 or the treatment probe 450 may be determined using one or more fiducials located on one of more of the probes as described herein. The one or more of the position or orientation of the one or more fiducials can be used to provide an indication to the user to move one or more of the probes.

Figure 4:
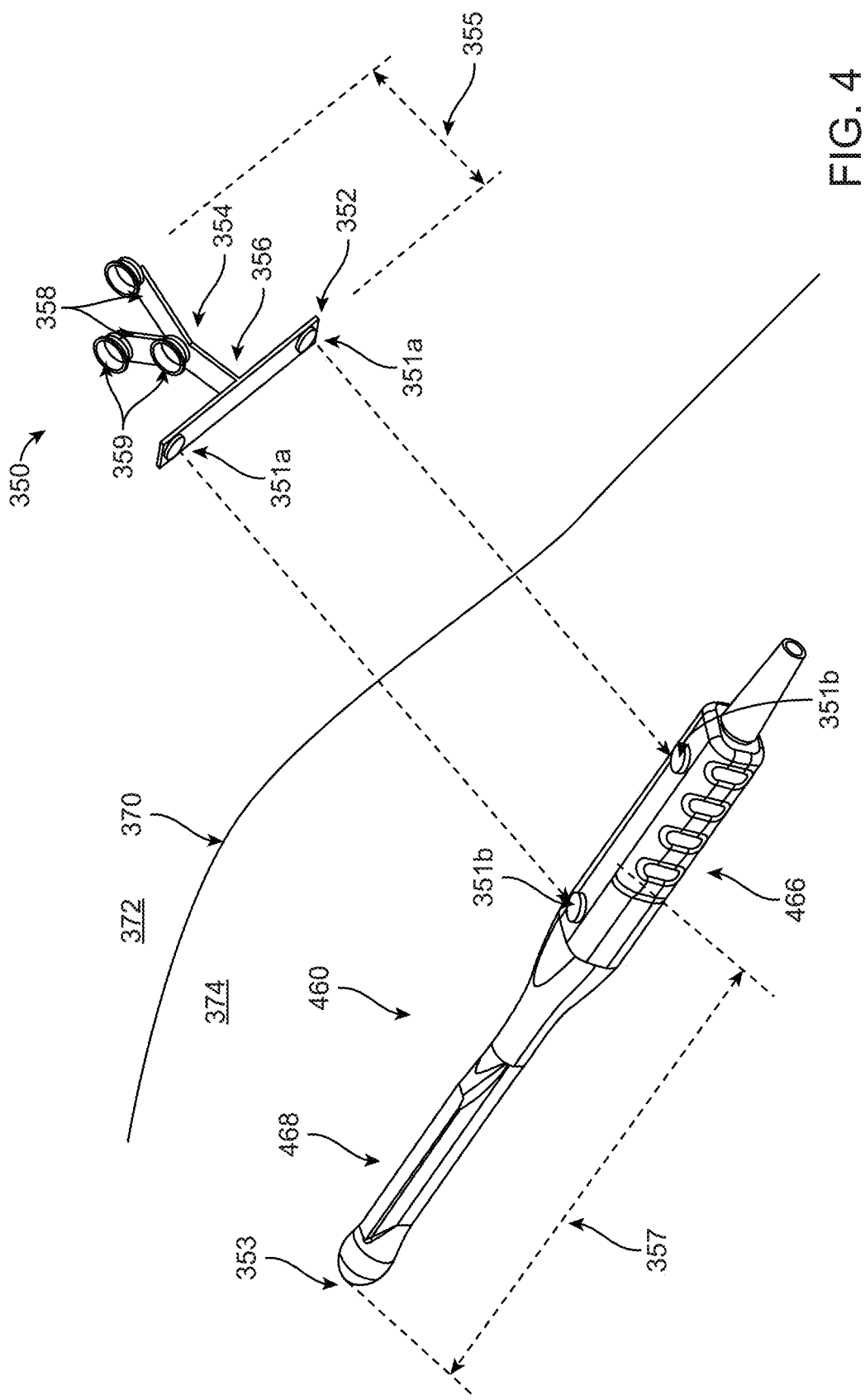
FIG. 4 shows a probe, such as an imaging probe, a couplable fiducial assembly, and a drape in accordance with some embodiments of the present disclosure.
Figure 5:
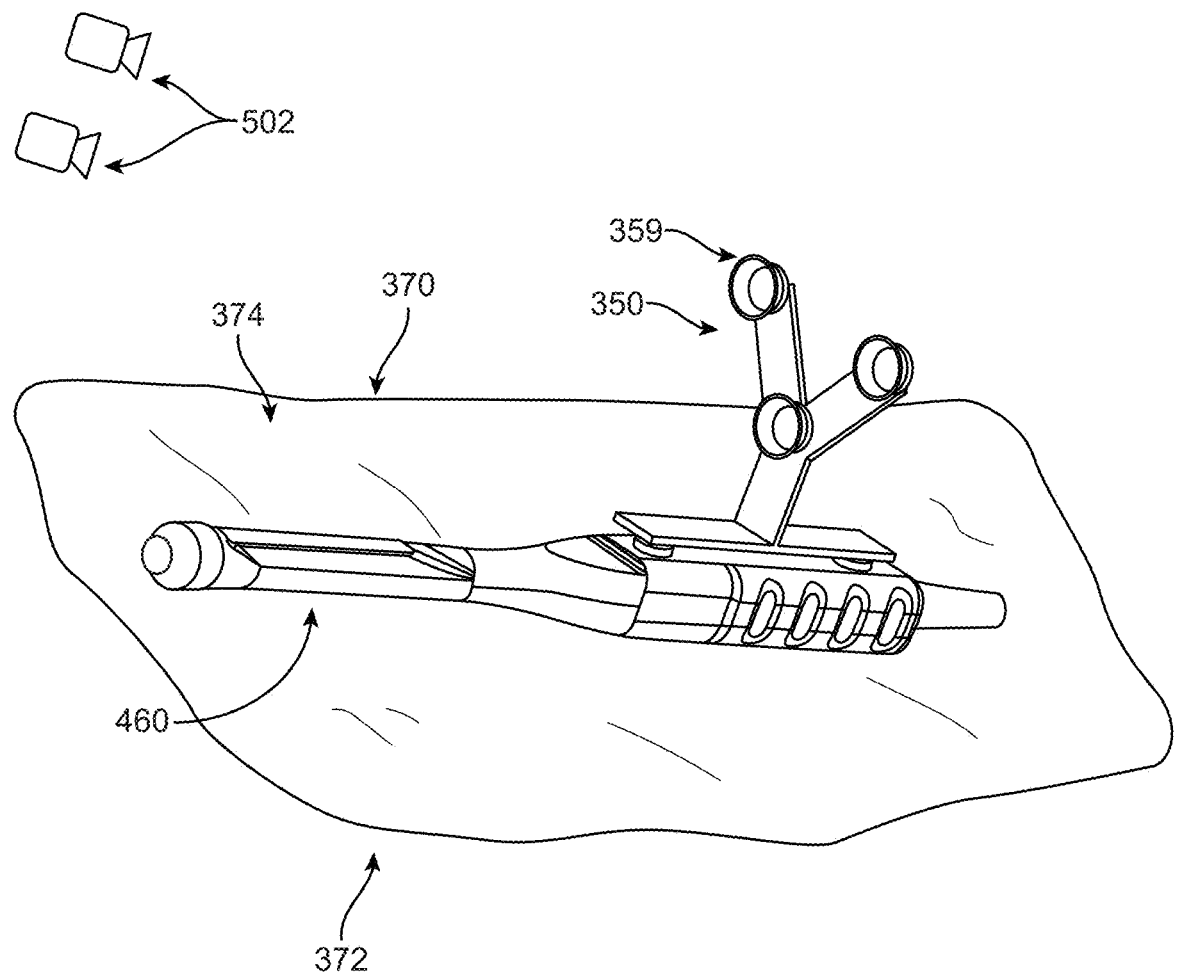
FIG. 5 shows a fiducial assembly coupled to a probe across a drape and one or more cameras, in accordance with some embodiments of the present disclosure.

FIGS. 4 and 5 show a probe, such as an imaging probe 460, a couplable fiducial assembly 350, and a sterile drape 370. The fiducial assembly 350 may be coupled to the imaging probe 460 across the drape 370. The fiducial assembly 350 may include a fiducial tree 354 extending from a base 352. The fiducial tree 354 may include one or more extensions that extend from the base 352 and/or each other to provide support for the one or more fiducials 359. In some embodiments, the fiducial tree 354 may include a trunk 356 and a plurality of branches 358. The probe such as imaging probe 460 may comprise a first portion 466 configured to remain outside the patient and a second portion 468 configured for insertion into the patient. In some embodiments, the fiducial assembly 350 is coupled to a housing of the first portion 466. In some embodiments, the proximal portion 466 coupled to fiducial assembly 350 remains outside the patient when the distal portion 468 has been inserted into the patient. In some embodiments, the material of the drape is located between the fiducial assembly 350 and the proximal portion 466 of the probe in order to maintain the sterile surgical field.

As depicted in FIG. 4, the fiducial assembly 350 may include a plurality of at least three fiducials 359 arranged on the tree 354. Although reference is made to a fiducial tree, any suitable structure can be used to support the one or more fiducials, such as a triangle, a square or polygon with the one or more fiducials at appropriate locations thereon. In some embodiments, the at least three fiducials 359 may be arranged so as to define a plane, e.g. not along a common line, and may comprise fiducials of a two dimensional fiducial as described herein. By arranging the fiducials so as to define a plane, one or more of a single camera, a stereo camera, or a plurality of cameras having different positions may be used to capture images of the fiducials 359. The difference in the location of the fiducials 359 in the images captured from the one or more cameras may be used to determine the position and orientation of fiducials, e.g. the pose of the one or more fiducials. In some embodiments, the plurality of three or more fiducials are located so as to define a plane and a two dimensional fiducial and may comprise any suitable combination of fiducials such as a two dimensional pattern. In some embodiments, the two dimensional fiducial is used to determine the position and orientation of the probe, for example the 6 degree of freedom (6 DOF) pose of the probe. The position and orientation of the two dimensional fiducial can be determined from one or more images of the two dimensional fiducial, as will be understood by one of ordinary skill in the art of machine vision and robotics.

When the fiducials 359 are in a known three-dimensional relationship with respect to the surgical probe they are attached to, then the position and orientation of the surgical probe may be determined based on the position and orientation of the fiducials. In some embodiments, the one more fiducials 359 comprise an offset 355 with respect to the base 352 or a probe structure such as the probe surface or elongate axis 461, which can be used to determine the position and orientation of the probe based on the position and orientation of the one or more fiducials and the offset 355. In some embodiments, offset 355 corresponds to a radial distance of the one or more fiducials 359 from the elongate axis 461 of the probe. In some embodiments, the one or more fiducials 359 comprise an offset 357 along elongate axis 461 with respect to a structure of the probe 460, such as a distal tip 353, which can allow the position and orientation of the structure of the probe to be determined in response to the position and orientation of the fiducial and the offset 357 along the elongate axis. In some embodiments, the position and orientation of the probe, i.e. the pose of the probe, is determined in response to the position and orientation of the one or more fiducials measured with the one or more cameras and the offset 357 along the elongate axis and the offset 355 transverse to the elongate axis 461.

The fiducials 359 may comprise passive fiducials that reflect or scatter light that is then captured by a camera system as described herein such as stereo camera system in order to determine the position and orientation of the fiducials. In some embodiments, the fiducials may comprise reflectors. Alternatively or in combination, the fiducials may may have a contrasting color that contrasts with surgical room. In some embodiments, the fiducials may comprise active fiducials that emit light that is then captured by the camera system as described herein. In some embodiments, the fiducials may reflect or emit infrared light or a nonvisible wavelength of light.

The fiducials may have many shapes. The fiducials may be round, square, triangular, or other shapes. In some embodiments, the fiducials may be spherical, cubicle, pyramidal, or another three-dimensional shape. In some embodiments, each of the fiducials 539 of a fiducial assembly 350 may be a different color or may emit light at a different wavelength.

In some embodiments, the fiducials may comprise light sources. In some embodiments, each of the light sources may emit light with a different on/off duty cycle or may have data encoded in light pulses emitted by the light sources in order for the cameras to identify each individual fiducial or set of fiducials separate from each other individual set of fiducials.

In some embodiments, the fiducial assembly 350 is coupled across the sterile drape 370 to a probe, such as the imaging probe 460. The sterile drape 370 separates the sterile area of the surgical field or operating room from the nonsterile area of the surgical field or operating room. Sterile drape 370 may be optically opaque or substantially optically opaque. In some embodiments, probes or other objects on one side of the sterile drape may not be visible from the other side of the sterile drape. Alternatively or in combination, at least a portion of the drape may comprise one or more transparent regions to allow viewing through the drape. In some embodiments, at least a portion of the drape is transparent to allow the one or more cameras to view the one or more fiducials through the transparent portion of the drape.

As depicted in FIG. 4, the fiducial assembly 350 is located on the sterile side 372 of the sterile drape 370. In some embodiments, the sterile side 372 may be located on the side of the sterile drape 370 that is visible to the stereo camera system while the nonsterile side 374 of the drape 370 may not be visible to the stereo camera system. In some embodiments, the fiducial assembly 350 should be on the visible side of the sterile drape 370, e.g. sterile side 372 and coupled to the surgical probe in a known spatial position and orientation relative to each other. Although reference is made to the one or more cameras located on the sterile side of the drape, in some embodiments the one or more cameras and the one or more fiducials are located on a non-sterile side of the drape, such that the one or more fiducials may be coupled to the probe without the drape in between the probe 450 and the base 352.

The one or more couplings 351 may couple the fiducial assembly 350 to the probe, across the sterile drape 370, in a known position and orientation relative to each other. The couplings may be configured to couple to each other in a single orientation across the drape. For example, in some embodiments, the couplings 351 may be magnetic couplings comprising one or more magnetic materials. In some embodiments, the magnetic couplings comprise rare earth magnets with polarities configured to attract and hold the couplings 351a on the fiducial assembly to the couplings 351b on the surgical probe across the drape 370. In some embodiments, the magnetic couplings are arranged to allow the one or more fiducials to be placed on the probe in a single orientation. In some embodiments, the couplings may be snaps such as socket and stud snaps wherein the coupling 351a on the fiducial assembly 350 are either a socket or a stud and the corresponding couplings 351b on the surgical probe are the other of a socket or a stud such that the sockets received the studs across the drape and snap together with the drape therebetween. In some embodiments, the stud and socket may be configured to account for the thickness of the drape 370 and the engagement between the stud and the socket. In some embodiments, the one or more couplings such as the stud and socket are dimensioned to engage each other with the drape therebetween without breaching the sterile barrier of the drape. In some embodiments, the couplings are dimensioned to engage each other across the drape without breaching the sterile barrier material of the drape, for example when the one or more couplings engage each other with the drape therebetween, or when the one or more couplings are separated from each other and release the drape.

In some embodiments, the coupling 351 may be arranged or keyed such that they couple the fiducial assembly 350 to the surgical probe in a single orientation. The coupling 351 may comprise one or more support structures such as protrusions, ribs, indentations or other structures to provide stability between the probe and the base.

With reference to FIG. 5, a fiducial assembly is shown coupled to a surgical probe 460 through a surgical drape 370 within a portion of a surgical facility with a camera system 502, such as a stereo camera system. The camera system 502 is located on the sterile side 374 of the drape 370 along with the fiducial assembly 350 and its corresponding fiducials 359. The camera system 502 may be placed at any suitable location and may be located outside the sterile field, for example. In some embodiments, the camera system 502 is located at a sufficient distance from the probe 460 such that it is outside of the sterile field and not sterile, for example. The camera system may comprise one or more stereoscopic cameras, single stereoscopic camera, a single camera, or a plurality of cameras. The sterile drape 370 may or may not be opaque to the wavelengths of light captured by the stereo camera system 350. The stereo camera system 502 may be arranged within the surgical room such that the cameras of the stereo camera system 502 have an unobstructed view of the fiducials 359. In some embodiments, the stereo camera system 502 may include a plurality of cameras such as three cameras, four cameras, five cameras, six cameras, or more cameras arranged in known spatial positions with known fields of view about the surgical area such that the fiducial assembly 350 and the corresponding fiducials 359 are visible to at least two cameras of the stereo camera system 502. In some embodiments, the plurality of cameras is arranged in known positions about the surgical area such that the fiducial assembly 350 and the corresponding fiducials 359 are visible to at least two cameras of the stereo camera system during alignment and use of the surgical probes.

Figure 6:
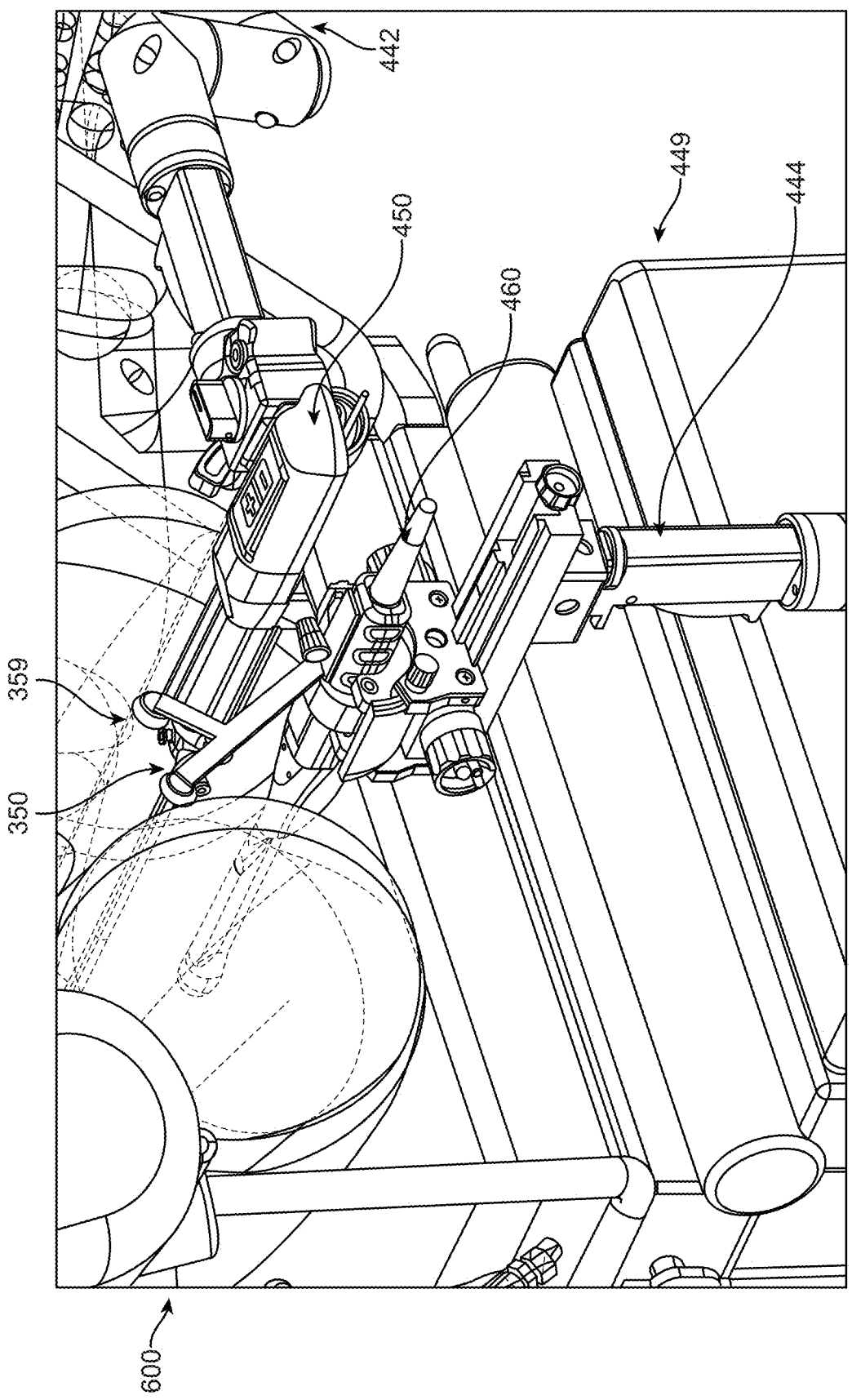
FIG. 6 shows a surgical probe and fiducial assemblies being used during a surgical procedure, in accordance with some embodiments of the present disclosure.

FIG. 6 shows surgical probes 450, 460 and fiducial assembly 350 being used during a surgical procedure on a patient 600. Although surgical drape is not shown in this figure, the surgical drape can be located between the imaging probe 460 and the one or more fiducials 359. The patient 600 is shown laying on their back on a patient support 449, which may be an operating table or other support. One or more arms, such as arms 442, 444 may be coupled to and extend from the patient support 449. In some embodiments, the arms comprise robotic arms. The treatment probe 450 may be coupled to a first arm 442 and the imaging probe 460 may be coupled to a second arm 444. In some embodiments, the first arm and the second arm comprise manually movable arms with brakes to lock the position and orientation of the probe. Alternatively or in combination, one or both of the first arm 442 and the second arm 444 may comprise robotic arms whose movements may be controlled by one or more computing devices operably coupled with the arms. The treatment probe 450 may comprise a device for removing or otherwise treating target tissue from a target site within a patient. In some embodiments, the treatment probe may be inserted into the patient through a urethra of the patient for treatment of the patient's prostate. The energy released from the treatment probe 450 may comprise any suitable energy as described herein. The treatment probe 450 may be configured to deliver energy from the treatment probe 450 to the target tissue with an amount of energy sufficient for removing the target tissue. For example, the treatment probe 450 may comprise an electrosurgical ablation device, a laser ablation device, a transurethral needle ablation device, a water jet ablation device, a steam ablation device, a high-intensity focused ultrasound (HIFU) device or any combination thereof.

The imaging probe 460 may be configured to deliver energy from the imaging probe 460 to the target tissue sufficient for imaging the target tissue. In some embodiments, the imaging probe may be inserted into the patient through the patient's rectum to image the patient transrectally, for example with a trans rectal ultrasound probe. The imaging probe 460 may comprise any suitable probe, such as an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six or seven degrees of freedom for each arm, to manipulate the treatment probe 450 and the imaging probe 460, respectively. The treatment system 400 may be used to perform tissue resection in an organ of a patient, such a prostate of a patient.

The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. Although omitted from FIG. 6, as discussed herein, the first arm 442 and the second arm 444 may be covered in one or more sterile drapes to provide a sterile operating environment, keep the arms clean, and reduce risks of damaging the arms.

The imaging probe 460 includes a fiducial assembly 350. The fiducial assembly 350 is coupled to the imaging probe 460 and includes a fiducial tree extending from a base. The fiducial tree includes extensions that extend from the base to provide support for the fiducials 359. In the embodiment depicted in FIG. 6, the fiducial tree may include a trunk and two branches, although other configures are contemplated, such as each fiducial extending from a corresponding individual extension or multiple fiducials on a single branch. The fiducial assembly 350 includes three fiducials 359 arranged on the tree: one at the intersection of the trunk with the branches and one at the distal end of each of the two branches. The fiducials 359 are arranged on the fiducial assembly 350 in a known arrangement and in a known three-dimensional relationship with the imaging probe to which they are attached. The known arrangement may be based on the shape of the fiducial assembly 350. Based on the known arrangement, an imaging system, such as the stereo camera system 502, may be used to image the fiducials and determine the location and orientation of the imaging probe based on the position and orientation of the fiducials and the known spatial relationship between the fiducials and the imaging probe 460. A similar fiducial assembly may be coupled to the treatment probe 450 to determine the location and orientation of the treatment probe 450, as discussed herein.

Figure 7:
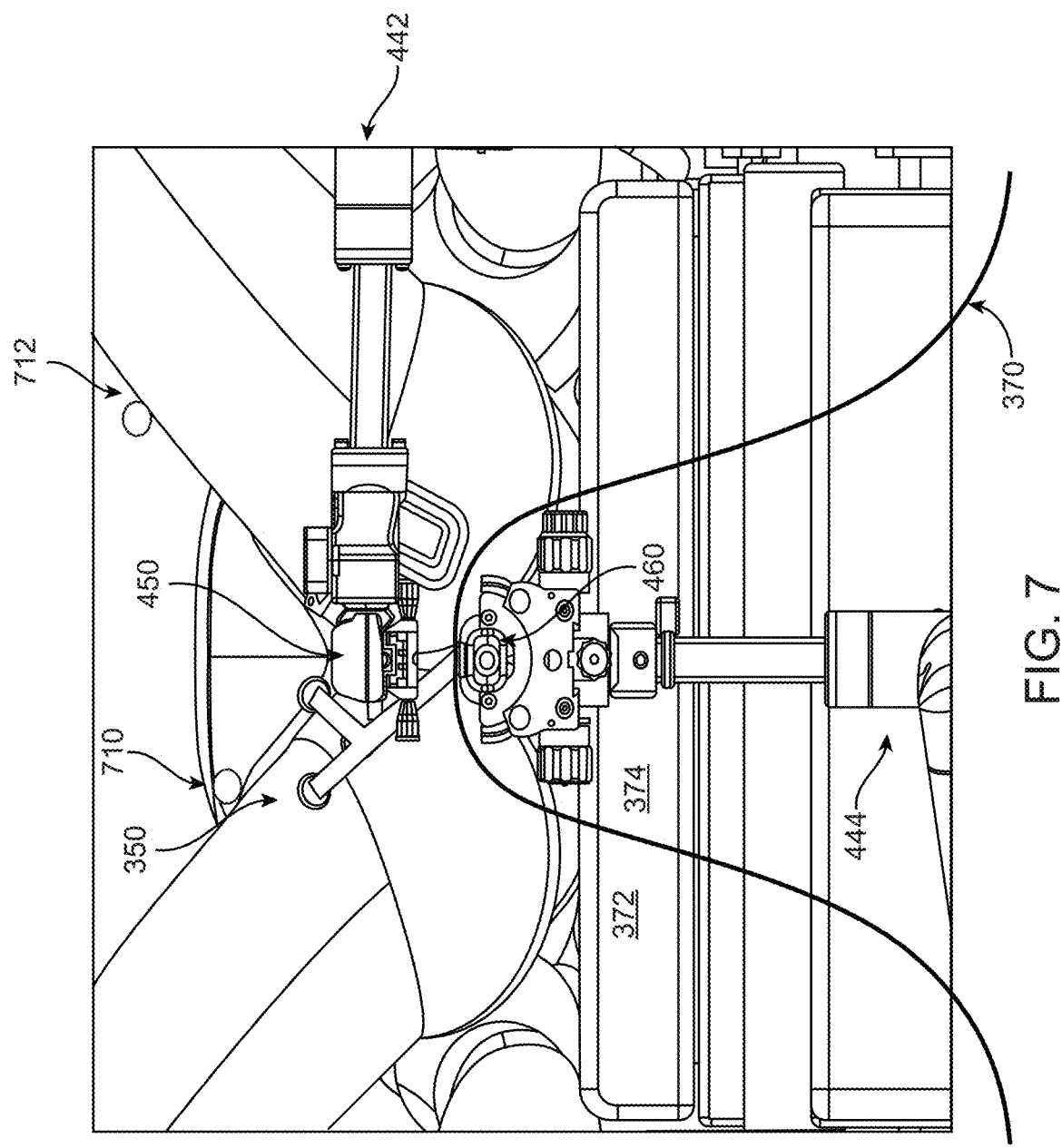
FIG. 7 shows a surgical probe and fiducials being used with a sterile drape during a surgical procedure, in accordance with some embodiments of the present disclosure.

FIG. 7 shows surgical probes 450, 460 and fiducial assembly 350 being used during a surgical procedure on a patient 600 with a surgical drape 370 and patient fiducials 710 and 712. The patient 600 is laying on their back on a patient support 449, which may be an operating table or other support. One or more arms, such as robotic arms 442, 444 maybe coupled to and extend from the patient support 449. A sterile drape 370 may be placed over the imaging probe 460. The imaging probe 460 may be on a non-sterile side 374 of the sterile drape 370. The sterile drape 370 may comprise a barrier that prevents contaminants from the nonsterile side of the drape from coming into contact with the sterile surgical site. For example, during transrectal ultrasound imaging, the sterile drape may aid in preventing fecal matter from coming into contact with sterile surgical site.

The fiducial assembly 350 may be located on a sterile side 372 of the sterile drape 370. The fiducial assembly 350 may be coupled across the sterile drape 370 to the imaging probe 460. In some embodiments, the fiducial assembly 350 may be magnetically or mechanically coupled to the imaging probe in a known spatial relationship on the sterile side 372 of the sterile drape 370. The fiducial assembly 350 includes a fiducial tree extending from a base. The fiducial tree includes extensions that extend from the base to provide support for the fiducials 359. The fiducial assembly 350 includes three fiducials 359 arranged on a tree: one at the intersection of the trunk with the branches and one at the distal end of each of the two branches. The fiducials 359 are arranged on the fiducial assembly 350 in a known spatial arrangement and in a known spatial three-dimensional relationship with the imaging probe to which they are attached. The known spatial arrangement may be based on the shape of the fiducial assembly 350. Using the known arrangement, an imaging system, such as stereo camera system 502 may be used to image the fiducials and determine the location and orientation of the imaging probe based on the position and orientation of the fiducials and the known spatial relationship between the fiducials and the imaging probe 460. A similar fiducial assembly may be coupled to the treatment probe 450 to determine the location and orientation of the treatment probe 450, as discussed herein.

As discussed herein, imaging probe 460 may be configured to deliver energy from the imaging probe 460 to the target tissue sufficient for imaging the target tissue. The imaging probe may be instead into the patient through the patient's rectum to image the patient transrectally. The imaging probe 460 may comprise any suitable probe such as ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees or seven of freedom, to manipulate the treatment probe 450 and the imaging probe 460, respectively. The treatment system 400 may be used to perform tissue resection in an organ of a patient, such a prostate of a patient.

The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues.

The treatment probe 450 may be coupled to a first arm 442 and the imaging probe 460 coupled to a second arm 444. One or both of the first arm 442 and the second arm 444 may comprise robotic arms whose movements may be controlled by one or more computing devices operably coupled with the arms. The treatment probe 450 may comprise a device for removing other otherwise treating target tissue from a target site within a patient. The treatment probe may be inserted into the patient through a urethra of the patient for treatment of the patient's prostate. The treatment probe 450 may be configured to deliver energy from the treatment probe 450 to the target tissue sufficient for removing the target tissue. For example, the treatment probe 450 may comprise an electrosurgical ablation device, a laser ablation device, a transurethral needle ablation device, a water jet ablation device, or any combination thereof.

In some embodiments, one or more fiducials 710, 712 may be placed on the patient to monitor the patient's movement, position, and orientation during the surgical procedure. Patient monitoring fiducials may be placed on limbs or other parts of the patient's anatomy. For example, patient fiducial 712 is placed on a patient's leg, such as the patient's thigh, in order to monitor the movement of the patient's leg during treatment. In some embodiments, a single camera may be used to monitor the patient's movement based on the movement of a patient fiducial. In some embodiments, a single camera may be used to monitor the patient's movement. The single camera can monitor for a change in the position of the fiducial in the image and determine that the patient has moved based on the movement of the fiducial within the image, for example without determining the three-dimensional spatial position and/or orientation of the fiducial. Alternatively, the patient fiducial may comprise a plurality of fiducials to determine the position and orientation of the patent at the location where the fiducial has been placed.

In some embodiments, one or more patient fiducials 710 may be placed on the patient's torso or hips in order to monitor movement of the patient's torso and hips during treatment. In some embodiments, a sterile drape 370 may be placed over the patient. In some embodiments, the patient fiducials are placed on a sterile drape located over the patient's body, such as on the drape over the patient's torso, hips, or legs. In some embodiments, the patient fiducials 710, 720 may comprise a fiducial assembly comprising a frame or base and at least three fiducials in a planar arrangement as described herein.

In some embodiments, the patient fiducials may be configured to allow an imaging system, such as a stereo camera system to determine the position and orientation of the patient fiducials during treatment. In some embodiments, the patient fiducials may be substantially similar to the fiducial assembly 350 described herein. In some embodiments, the coupling comprises a first coupling placed on the patient, for example with tape, and a second coupling on the base that engages the first coupling through a sterile drape as described herein.

In some embodiments, the fiducials as described herein may be used in tele proctoring. For example, the fiducial assemblies and patient fiducials may be used to determine the position and orientation and/or movement of the patient during surgery. This position, orientation, and movement information may be sent to a remote medical professional to conduct or monitor the procedure and to provide feedback or assistance during the procedure.

Figure 8:
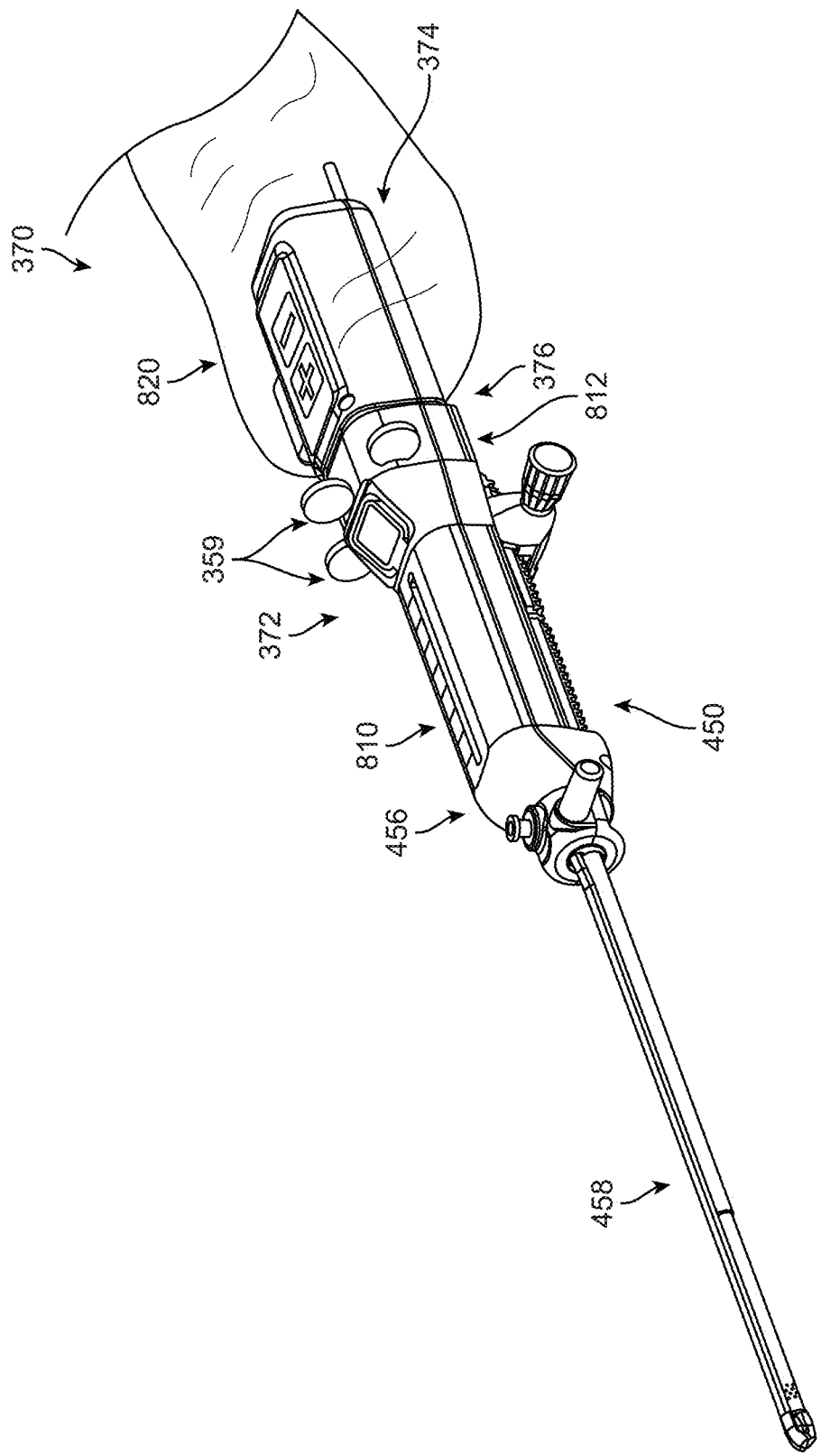
FIG. 8 shows a surgical probe with fiducials, in accordance with some embodiments of the present disclosure.

FIG. 8 shows a sterile treatment probe 450 with sterile fiducials 359 coupled to a disposable sterile housing 810 of a single use disposable treatment probe 450. The fiducials 359 may be directly coupled to or integral to the housing 810, which may comprise a shell portion 812. The fiducials 359 may extend from a surface of the disposable housing 810, e.g. from a shell portion of the housing. In some embodiments, the probe such as treatment probe 460 may comprise a first portion 456 configured to remain outside the patient and a second portion 458 configured for insertion into the patient. In some embodiments, the fiducial assembly 350 is coupled to a housing of the first portion 466. In some embodiments, the proximal portion 456 coupled to fiducial one or more fiducials 359 remains outside the patient when the distal portion 458 has been inserted into the patient.

In some embodiments, the treatment probe 450 comprises a hand piece that allows the user to manipulate the treatment probe while inserting the probe into the patient. In some embodiments, the treatment probe 450 is coupled to a reusable non-sterile instrument driver 820 supported with the arm as described herein.

The instrument driver may comprise any suitable device to drive the probe. In some embodiments, the instrument driver is mounted on the end of an arm as described herein. In some embodiments, the instrument driver 820 comprises one or more structures to drive the probe. In some embodiments, the one or more structures comprises one or more of a rotatable body, a lever, a pull wire, a gear, a linkage, a motor, a motor pack, or a transmission. While many instrument drivers can be used, examples of instrument drivers and instrument device manipulators suitable for use in accordance with the present disclosure are described in PCT/US2021/070760, filed on Jun. 23, 2021, entitled "INTEGRATION OF ROBOTIC ARMS WITH SURGICAL PROBES", published as WO2021263276, the entire disclosure of which has been previously incorporated herein by reference.

The treatment probe 450 may comprise any suitable treatment probe. In some embodiments, the treatment probe 450 comprises internal gears and linkages to move the energy source in response to rotation of components of the instrument driver 820, so as to rotate and translate the energy source in accordance with instructions from the processor as described herein. While many treatment probes can be used, examples of suitable treatment probes comprising handpieces are described in PCT/US2015/048695, filed Sep. 5, 2015, entitled "PHYSICIAN CONTROLLED TISSUE RESECTION INTEGRATED WITH TREATMENT MAPPING OF TARGET ORGAN IMAGES", published as WO2016037137, the entire disclosure of which has been previously incorporated herein by reference.

As depicted in FIG. 8, the disposable shell portion of the housing 810 may include at least three fiducials 359 arranged thereon. In some embodiments, the fiducials 359 may be arranged in a plane as described herein. By arranging the fiducials to define a plane a stereo camera or a plurality of cameras having different positions may be used to capture images of the fiducials 359. The difference in the location of the fiducials 359 in the images captured from the stereo camera or other cameras may be used in order to determine the position and orientation of fiducials as described herein. If the fiducials 359 are in a known three-dimensional relationship with the surgical probe they are attached to, then the position and orientation of the surgical probe may be determined based on the position and orientation of the fiducials.

The fiducials 359 may comprise passive fiducials that reflect light that is then captured by a stereo camera system in order to determine the position and orientation of the fiducials. In some embodiments, the fiducials may be reflectors. In some embodiments, the fiducials may not be reflectors but may have a contrasting color that contrasts with surgical room. In some embodiments, the fiducials may be active fiducials that emit light that is then captured by the stereo camera system. In some embodiments, reflect or emit infrared light or a nonvisible wavelength of light.

The fiducials may have many shapes. The fiducials may be round, square, triangular, or other shapes. In some embodiments, the fiducials may be spherical, cubicle, pyramidal, or another three-dimensional shape. In some embodiments, each of the fiducials 539 of a fiducial assembly 350 a different color or may emit light at a different wavelength. In some embodiments, the fiducials may be light sources and each of the light sources may emit light with a different on/off duty cycle or may have data encoded in light pulses emitted by the light sources in order for the cameras to identify each individual fiducial separate from each other individual fiducial.

In some embodiments, the shell portion of the housing 810 is coupled across the sterile drape 370 to the instrument driver 820. The sterile drape 370 separates the sterile area 372 of the surgical field or operating room from the non-sterile area 374 of the surgical field or operating room. In some embodiments, the sterile drape may include a fenestration 376 to couple the housing 810 to the instrument driver 820 across the sterile drape. The fenestration 376 may be an aperture through the sterile drape 370 from the nonsterile side 374 to the sterile side 372. In some embodiments, a portion of the instrument driver 820 of the surgical probe 450 passes through the fenestration 376 and couples with the sterile disposable shell 810. In some embodiments, a perimeter of the fenestration 376 is captured by the sterile shell 810 and the instrument driver 820 in order to separate the sterile side 372 from the nonsterile side 374 of the sterile drape 370. In some embodiments, capturing the perimeter of the fenestration 376 closes the fenestration 376 and aids in preventing contamination passing from the nonsterile side 374 to the sterile side 372.

FIGS. 9A and 9B show a surgical probe 450 with a couplable fiducial assembly 350. The fiducial assembly 350 may be coupled to the instrument driver 820 of the treatment probe 450 across the drape 370. The fiducial assembly 350 may include a fiducial tree 354 extending from a base 352. The fiducial tree 354 may include one or more extensions that extend from the base 352 and/or each other to provide support for the fiducials 359. In some embodiments, the fiducial tree 354 may include a trunk and a plurality of branches. The fiducial assembly 350 may include at least three fiducials 359 arranged on the tree 354. In some embodiments, the fiducials 359 may be arranged so as to define a plane, for example not extending along a straight line. A stereo camera or a plurality of cameras having different positions may be used to capture images of the fiducials 359 to determine the position and orientation of the treatment probe 450.

The fiducials 359 may be passive fiducials that reflect light that is then captured by a stereo camera system to determine the position and orientation of the fiducials. In some embodiments, the fiducials may be reflectors. In some embodiments, the fiducials may not be reflectors but may have a contrasting color that contrasts with surgical room. In some embodiments, the fiducials may be active fiducials that emit light that is then captured by the stereo camera system. In some embodiments, reflect or emit infrared light or a nonvisible wavelength of light.

The fiducials 359 may have many shapes. The fiducials may be round, square, triangular, or other shapes. In some embodiments, the fiducials may be spherical, cubicle, pyramidal, or another three-dimensional shape. In some embodiments, each of the fiducials 539 of a fiducial assembly 350 a different color or may emit light at a different wavelength. In some embodiments, the fiducials may be light sources and each of the light sources may emit light with a different on/off duty cycle or may have data encoded in light pulses emitted by the light sources in order for the cameras to identify each individual fiducial separate from each other individual fiducial.

In some embodiments, the disposable sterile shell 810 is coupled across the sterile drape 370 to the instrument driver 820. The sterile drape 370 separates the sterile area 372 of the surgical field or operating room from the nonsterile area 374 of the surgical field or operating room. In some embodiments, the sterile drape may include a fenestration 376 to couple the shell 810 to the instrument driver 820 across the drape. The fenestration 376 may be an aperture through the sterile drape 370 from the nonsterile side 374 to the sterile side 372. In some embodiments, a portion of the instrument driver 820 of the treatment probe 450 passes through the fenestration 376 and couples with the sterile disposable shell 810. In some embodiments, a perimeter of the fenestration 376 may be captured between the sterile shell 810 and the instrument driver 820 in order to separate the sterile side 372 from the nonsterile side 374 of the sterile drape 370. In some embodiments, capturing the perimeter of the fenestration 376 closes the fenestration 376 and aids in preventing contamination passing from the nonsterile side 374 to the sterile side 372.

In some embodiments, the fiducial assembly 350 is coupled across the sterile drape 370 to a surgical probe, such as the treatment probe 450. As depicted in FIGS. 9A and 9B, the fiducial assembly 350 is on the sterile side 372 of the sterile drape 370.

The one or more couplings 351 may couple the fiducial assembly 350 to the surgical probe, across the sterile drape 370, and a known position and orientation relative to each other. The couplings may be configured to couple to each other in a single orientation across the drape. For example, in some embodiments, the couplings 351 may be magnetic couplings, such as rare earth magnets with polarities configured to attract and hold the couplings 351*a* on the fiducial assembly to the couplings 351*b* on the surgical probe across the drape 370. In some embodiments, the couplings may be snaps such as socket and stud snaps wherein the coupling 351*a* on the fiducial assembly 350 are either a socket or a stud and the corresponding couplings 351*b* on the surgical probe are the other of a socket or a stud such that the sockets received the studs across the drape and snap together with the drape located between the couplings 351*a* and the couplings 351*b*. In some embodiments, the stud and socket may be configured to account for the thickness of the drape 370 and the engagement between the stud and the socket. In some embodiments, the one or more couplings such as the stud and socket are dimensioned to engage each other with the drape therebetween without breaching the sterile barrier of the drape. In some embodiments, the couplings are dimensioned to engage each other across the drape without breaching the sterile barrier material of the drape, for example when the one or more couplings engage each other with the drape therebetween, or when the one or more couplings are separated from each other and release the drape. In some embodiments, the stud has a diameter that is greater than the diameter of the socket to which is couples. In some embodiments, that stud may not interfere with the socket without the drape therebetween.

In some embodiments, the coupling 351 may be arranged or keyed such that they couple the fiducial assembly 350 to the surgical probe in a single orientation.

With reference to FIG. 9B, a fiducial assembly is shown coupled to a surgical probe 460 through a surgical drape 370 within a portion of a surgical facility with a stereo camera system 502. The stereo camera system 502 may be located on the sterile side 374 of the drape 370 along with the fiducial assembly 350 and its corresponding fiducials 359. The stereo camera system 502 may be arranged within the surgical room such that the cameras of the stereo camera system 502 have an unobstructed view of the fiducials 359.

Figure 10A:
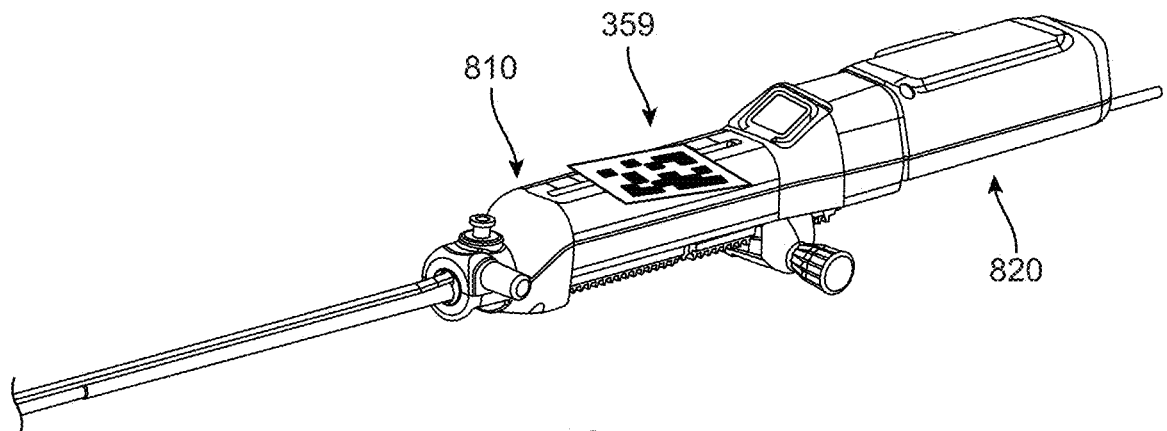
FIG. 10A shows a surgical probe with two-dimensional fiducials, in accordance with some embodiments of the present disclosure.
Figure 10B:
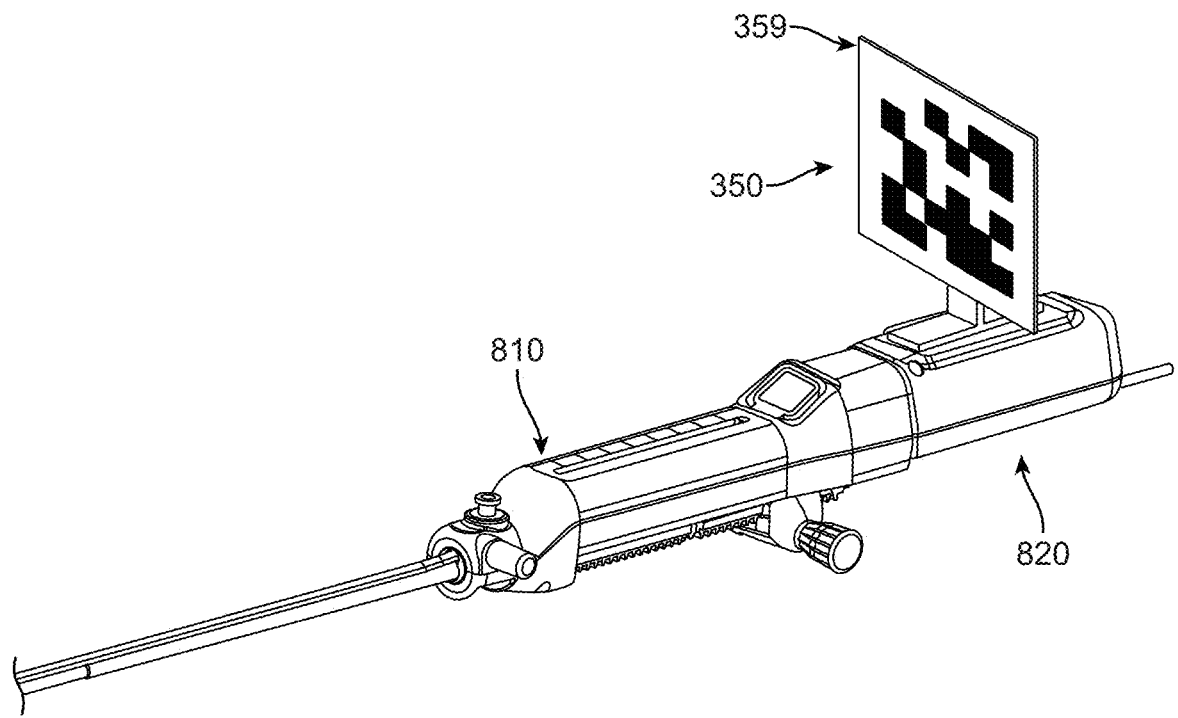
FIG. 10B shows a surgical probe with two-dimensional fiducials, in accordance with some embodiments of the present disclosure.

FIGS. 10A and 10B show examples of a surgical probe in which the one or more fiducials comprises two-dimensional fiducials. In some embodiments, a two-dimensional usual may be used in order to determine the three-dimensional position and orientation of a surgical probe. A two-dimensional fiducial may comprise a two-dimensional pattern such as one or more of two-dimensional bar code or a QR code. An example of a suitable two-dimensional fiducial is the AprilTag, which is commercially available from the App Store of Apple, Inc. and Google Play. The two-dimensional fiducial may be integrated directly into the surgical probe or coupled to the probe as described herein. For example, as depicted in FIG. 10A, a two-dimensional fiducial 359 may be printed or embedded directly onto the sterile shell 810 and a known size and orientation. A two-dimensional fiducial printed directly on a sterile portion of a surgical probe such as the sterile shell 810 may be directly viewable by one or more cameras within the operating room. The two dimensional fiducial can be used to determine the position and orientation of the probe, for example the 6 degree of freedom (6 DOF) pose of the probe.

In some embodiments, a two-dimensional fiducial 359 may be part of a fiducial assembly 350. FIG. 10B depicts a fiducial assembly 350 coupled to an instrument driver 820. The fiducial assembly 350 may include one or more supports are extensions extending from a base. The extensions may support the two-dimensional fiducial 359. In some embodiments the two-dimensional fiducial may be printed directly on or formed on the fiducial assembly 350. As discussed herein, the fiducial assembly 350 may be couplable across a drape 370 two the surgical probe, such as shown and described herein with respect to FIGS. 7, 8, 9A, and 9B.

A benefit of a two-dimensional fiducial that a single camera may be used to determine the three-dimensional position and orientation of the fiducial and thereby determine the position and orientation of the surgical probe to which the two-dimensional fiducial is attached. In a system that uses two-dimensional fiducials, the position field-of-view, and other properties of the camera system are known along with the size and shape of the fiducial. By using properties of the camera system and the fiducial, an image of the fiducial taken with the camera system may be analyzed to determine the position and orientation of the fiducial. If the spatial relationship between the two-dimensional fiducial and the surgical probe to which it is attached is known, then the position and orientation of the surgical probe may also be determined.

Figure 11:
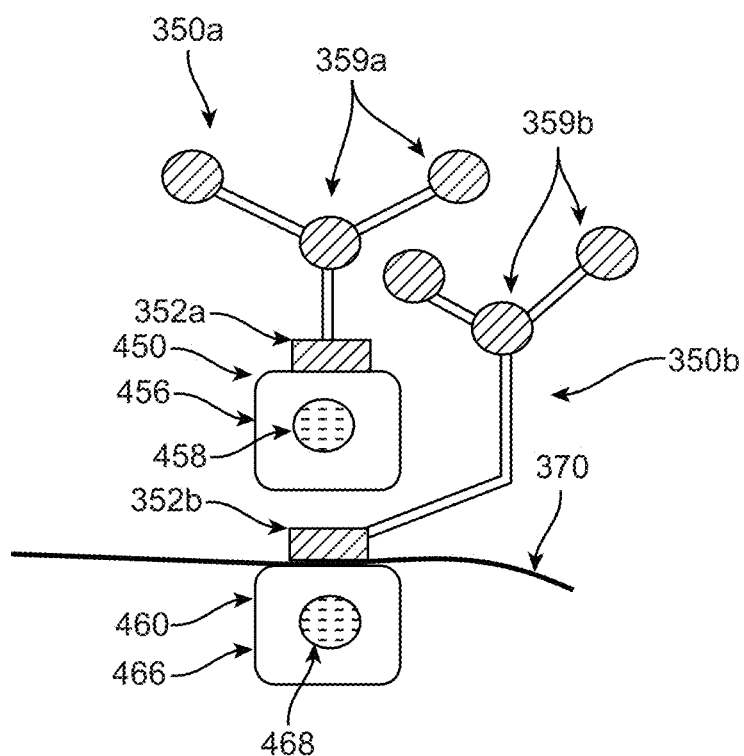
FIG. 11 shows a plurality of fiducials within a field of view of one or more cameras, in which a first one or more fiducials is coupled to a first probe and a second one or more fiducials is coupled to a second probe.

FIG. 11 shows a plurality of fiducials within a field of view of one or more cameras, in which a first one or more fiducials 359a is coupled to a first probe 450 as described herein and a second one or more fiducials 359b is coupled to a second probe 460 as described herein. In some embodiments, first fiducial assembly 350a is coupled to first probe 450 as described herein, and the first fiducial assembly 350a may comprise any suitable components of fiducial assembly 350 as described herein, such as branches, a base, and a coupling. In some embodiments, a second fiducial assembly 350b is coupled to a second probe 460 as described herein, and the second fiducial assembly 350b may comprise any suitable components of fiducial assembly 350 as described herein, such as branches, a base and a coupling. The first one or more fiducials 359a may comprise any suitable features of one or more fiducials 359 as described herein. The second one or more fiducials 359b may comprise any suitable features of one or more fiducials 359 as described herein.

While the first one or more fiducials and the second one or more fiducials can be configured in many ways, in some embodiments the first probe 450 comprises a sterile treatment probe and the second probe 460 comprises a non-sterile imaging probe such as a transrectal imaging probe. In some embodiments, the first one or more fiducials 350a have been sterilized and are attached to the treatment probe 450, for example without a drape between the first one or more fiducials and the treatment probe. In some embodiments, the second one or more fiducials 350b is coupled to the second probe 460 across the drape, for example coupled to the housing on the proximal portion 466. In some embodiments, the second fiducial assembly 350b comprises a base 352b, which couples to the housing of the proximal portion 466 with the drape 370 extending therebetween. The distal portion 468 of the imaging probe is configured to be inserted into the patient as described herein. In some embodiments, the treatment probe 450 is located above the imaging probe 450, and the distal portion 458 of the treatment probe 450 is inserted into the patient.

The first one or more fiducials and the second one or more fiducials can be imaged in any suitable way as described herein. Work in relation to the present disclosure suggests that it can be helpful to have the first one or more fiducials and the second one or more fiducials within the field of view of the one or more cameras, such that both of the one or more fiducials can be captured in a single image frame. Capturing both the first fiducial and the second fiducial in the same image frame with the same sensor may decrease errors in determining the relative position and orientation of the probes, for example. This approach can provide relative difference information between the probes, such as a differential orientation between the probes. In some embodiments, it is sufficient to determine the relative orientation of the probes, which can be used to provide an output to a user to adjust one or more of the probes as described herein. In some embodiments, a single camera is used to determine the relative orientation between the two probes. In some alternative embodiments, the one or more cameras comprises a stereoscopic camera or a plurality of cameras arranged in a stereoscopic configuration to provide the position and orientation of each of the probes, for example the 6 degree of freedom (6 DOF) position and orientation of each of the probes.

In some embodiments, the first one or more fiducials and the second one or more fiducials are imaged with a single camera, and the relative orientation of the first probe and the second probe determined in response to locations of the first one or more fiducials and the second one or more fiducials in one or more images from the cameras.

Figure 12:
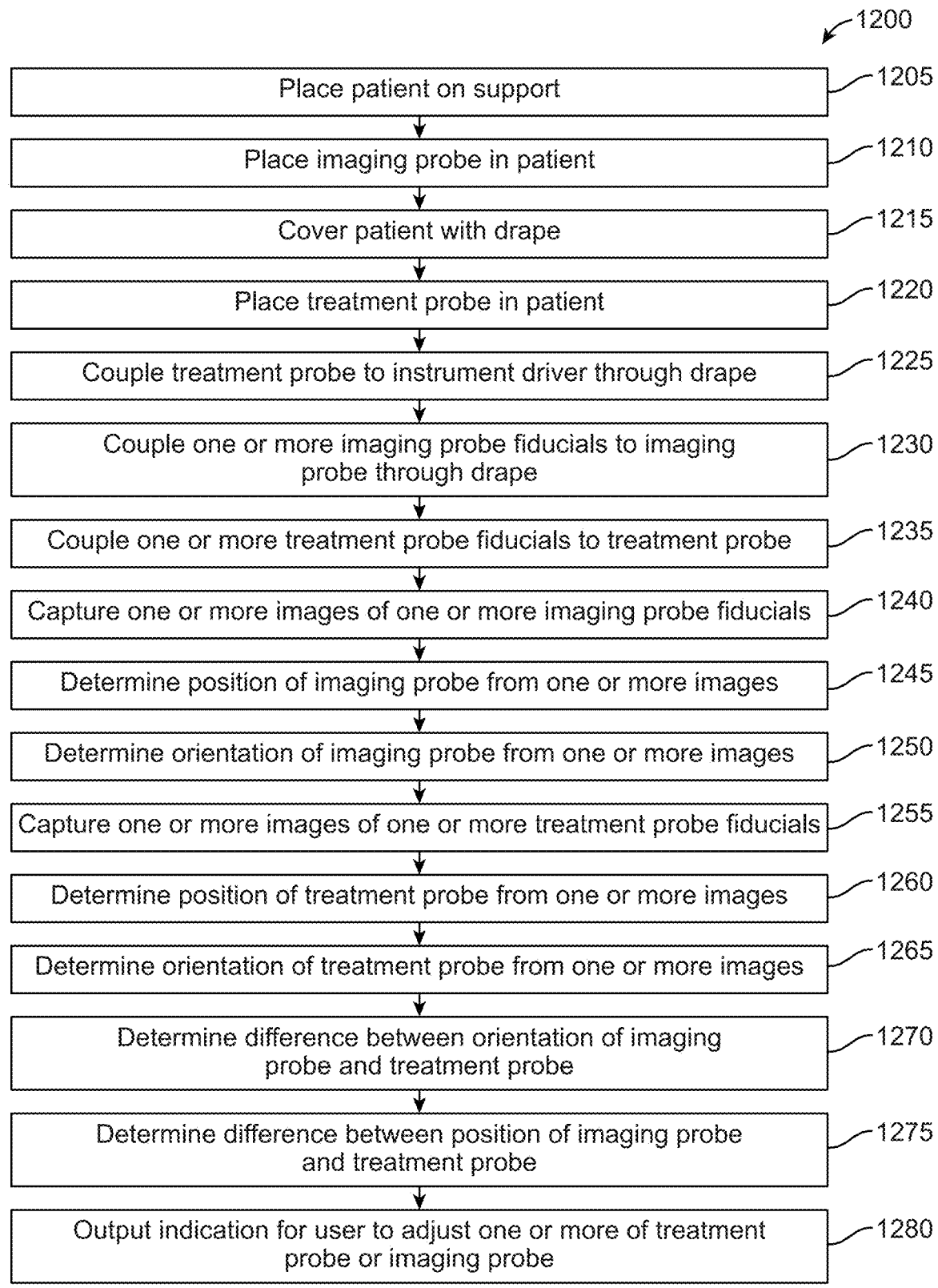
FIG. 12 shows a fiducial method, in accordance with some embodiments of the present disclosure.

FIG. 12 shows a fiducial method 1200.

At a step 1205, the patient is placed on support.
At a step 1210, the imaging probe is placed in the patient.
At a step 1215, the patient is covered with a drape.
At a step 1220, the treatment probe is placed in the patient.
At a step 1225, the treatment probe is coupled to the instrument driver across the drape, e.g. through an opening in the drape.
At a step 1230, one or more imaging probe fiducials is coupled to the imaging probe across the drape, e.g. through a material of the drape.
At a step 1235, one or more treatment probe fiducials is coupled to the treatment probe.
At a step 1240, one or more images of one or more imaging probe fiducials is captured with one or more cameras as described herein.
At a step 1245, a position of the imaging probe is determined from the one or more images.
At a step 1250, an orientation of the imaging probe is determined from the one or more images.
At a step 1255, one or more images of one or more treatment probe fiducials is captured with one or more cameras.
At a step 1260, a position of the treatment probe is determined from the one or more images.
At a step 1265, an orientation of the treatment probe from the one or more images.
At a step 1270, a difference between orientation of imaging probe and treatment probe is determined.
At a step 1275, a difference between a position of the imaging probe and the treatment probe is determined.
At a step 1280, an indication is output to a user interface for user to adjust one or more of treatment probe or imaging probe. The indication may comprise any suitable indication such as one or more of an alert, a notification, a message on a display, a notification on a display, a pop up screen, a color on a display, an audible alert, or a haptic communication, for example.

Although FIG. 12 shows a method 1200 in accordance with some embodiments, one of ordinary skill in the art will recognize many adaptations and variations. The steps can be performed in any order. Some of the steps can be combined, and some steps may comprise sub-steps of other steps. Some of the steps can be omitted and some of the steps repeated.

The processor as described herein can be configured to perform one or more steps of the method 1200.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising".

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A fiducial system for use with a drape comprising: a fiducial assembly configured to couple to the probe across the drape with a fixed orientation and offset relative to an elongate axis of a probe, the fiducial assembly comprising: a base; a coupling attached to the base and configured to couple the fiducial assembly to the probe across the drape; and one or more fiducials attached to the base.

Clause 2. The fiducial system of clause 1, wherein the one or more fiducials comprises a two-dimensional fiducial.

Clause 3. The fiducial system of clause 2, wherein the one or more fiducials comprises a two-dimensional fiducial array.

Clause 4. The fiducial system of clause 2, wherein two dimensional fiducial comprise a first fiducial, a second fiducial, and a third fiducial arranged along a plane.

Clause 5. The fiducial system of clause 1, wherein the fiducial assembly further comprises: a fiducial tree extending from the base, the one or more fiducials attached to branches of the fiducial tree.

Clause 6. The fiducial system of clause 1, wherein the one or more fiducials comprise light sources.

Clause 7. The fiducial system of clause 1, wherein the one or more fiducials comprise light reflectors.

Clause 8. The fiducial system of clause 1, wherein the one or more fiducials comprise a single two-dimensional fiducial.

Clause 9. The fiducial system of clause 1, wherein the probe comprises one or more of an imaging probe or a treatment probe.

Clause 10. The fiducial system of clause 1, wherein the one or more fiducials is configured to be located on a sterile side of the drape and at least portion of the probe is configured to be located on a non-sterile side of the drape.

Clause 11. The fiducial system of clause 1, wherein the one or more fiducials is configured to be located on a first side of the drape at least a portion of the surgical probe is configured to be located on a second side of the drape.

Clause 12. The fiducial system of clause 1, wherein the coupling couples the surgical drape, the probe, and the fiducial assembly together.

Clause 13. The fiducial system of clause 1, wherein a first portion of the coupling is located on the probe and a second portion of the coupling is located on the fiducial assembly, the first portion configured to couple to the second portion with the drape between the first portion and the second portion.

Clause 14. The fiducial system of clause 13, wherein the coupling comprises magnetic couplings.

Clause 15. The fiducial system of clause 1, wherein the coupling comprises a snap coupling.

Clause 16. The fiducial system of clause 1, wherein the coupling comprises a stud portion located one of the probe or the fiducial assembly and a second portion including a socket located on a second one of the probe or the fiducial assembly.

Clause 17. The fiducial system of clause 1, wherein the coupling is configured to couple the fiducial assembly to the probe in a single orientation.

Clause 18. The fiducial system of clause 17, wherein the coupling is configured to couple the fiducial assembly to the probe at a single position and the single orientation with respect to the probe.

Clause 19. The fiducial system of clause 18, wherein the coupling and the one or more fiducials are configured to couple the one or more fiducials to the probe with a fixed offset distance from the elongate axis and a fixed location along the elongate axis.

Clause 20. The fiducial system of clause 19, wherein the fixed location along the elongate axis corresponds to a fixed distance between the fixed location and a distal tip of the probe.

Clause 21. The fiducial system of clause 1, further comprising a processor configured to determine a position and an orientation of the probe in response to a position and an orientation of the one or more fiducials.

Clause 22. The fiducial system of clause 21, further comprising: one or more cameras coupled to the processor, the one or more cameras comprising a field of view to generate an image of the one or more fiducials coupled to the probe across the drape; wherein the processor is configured to process the image to determine the position and orientation of the probe coupled to the one or more fiducials across the drape.

Clause 23. The fiducial system of clause 22, further comprising a second probe comprising a second one or more fiducials within the field of view of the one or more cameras and wherein the processor is configured to determine a position and an orientation of the second probe.

Clause 24. The fiducial system of clause 23, wherein the one or more cameras comprises a single camera and the processor is configured to determine a difference between the orientation of the probe and the orientation of the second probe.

Clause 25. The fiducial system of clause 22, further comprising a second probe comprising an orientation sensor coupled to the processor and wherein the processor is configured to determine an orientation of the second probe relative to the probe in response to data from the orientation sensor of the second probe and the one or more fiducials.

Clause 26. The fiducial system of clause 25, wherein the probe comprises a trans rectal ultrasound probe and the second probe comprises a treatment probe.

Clause 27. A system for use with a drape comprising: a probe comprising a sterile portion configured to be located on a sterile side of a drape; an instrument driver configured to be on a non-sterile portion side of the surgical drape, wherein the sterile portion and the instrument manipulator are couplable to each other across the surgical drape; and one or more sterile fiducials in a fixed spatial relationship with the sterile portion of the probe.

Clause 28. The system of clause 27, wherein the one or more fiducials is couplable to the probe in the fixed special relationship.

Clause 29. The fiducial system of clause 28, wherein the one or more fiducials comprises a two-dimensional fiducial.

Clause 30. The fiducial system of clause 29, wherein the one or more fiducials comprises a two-dimensional fiducial array.

Clause 31. The fiducial system of clause 29, wherein two dimensional fiducial comprise a first fiducial, a second fiducial, and a third fiducial arranged along a plane.

Clause 32. The system of clause 27, wherein the fiducial assembly further comprises: a fiducial tree extending from the base, the one or more fiducials attached to branches of the fiducial tree.

Clause 33. The system of clause 27, wherein the one or more fiducials comprise light sources.

Clause 34. The system of clause 27, wherein the one or more fiducials comprise light reflectors.

Clause 35. The system of clause 27, wherein the one or more fiducials comprise a single two-dimensional fiducial.

Clause 36. The system of clause 27, wherein the one or more fiducials is configured to be located on a sterile side of the surgical drape.

Clause 37. The system of clause 27, wherein the surgical probe comprises one or more of an imaging probe or a treatment probe.

Clause 38. The system of clause 27, wherein a first portion of the one or more couplings is on the surgical probe and a second portion of the one or more coupling is located on the fiducial assembly.

Clause 39. The system of clause 38, wherein the one or more couplings comprise magnetic couplings.

Clause 40. The system of clause 27, wherein the one or more couplings comprise snap couplings.

Clause 41. The system of clause 27, wherein the one or more couplings comprise a stud portion on one of the surgical probe or the fiducial assembly and a second portion including a socket on a second one of the surgical probe or the fiducial assembly.

Clause 42. The system of clause 27, wherein the one or more couplings are configured to couple the fiducial assembly to the probe in a single orientation.

Clause 43. The system of clause 27, wherein the couplings couple the surgical drape, the surgical probe, and the fiducial assembly together.

Clause 44. The system of clause 27, wherein the one or more fiducials is affixed to the sterile portion.

Clause 45. The system of clause 27, wherein the one or more fiducials extends directly form the sterile portion.

Clause 46. The system of clause 45, wherein the one or more fiducials includes three fiducials in a plane.

Clause 47. The system of clause 27, wherein the one or more fiducials are sterile and integrated with the sterile portion with a similar material.

Clause 48. The system of clause 27, wherein the one or more fiducials comprises a sterile fiducial formed on the sterile portion.

Clause 49. The system of clause 27, wherein the one or more fiducials comprises a fiducial printed on the sterile portion.

Clause 50. The system of clause 27, wherein the sterile portion comprises a sterile shell of the surgical probe and the one or more fiducials extend from the sterile shell.

Clause 51. The system of clause 27, wherein the instrument driver comprises one or more structures to engage the probe, the one or more structures comprising one or more of a rotatable body, a lever, a pull wire, a gear, a linkage, a motor, a motor pack, or a transmission.

Clause 52. The system of clause 27, wherein the probe is configured to couple to the instrument driver across the drape with an opening through the drape.

Clause 53. The system of clause 27, wherein the probe comprises a sterile, single use, disposable probe and wherein the instrument driver comprises a non-sterile reusable component.

Clause 54. The system of clause 27, wherein the one or more sterile fiducials is coupled to the instrument driver across the drape.

Clause 55. The system of clause 27, further comprising a processor, wherein the processor is configured to determine the position and the orientation of the probe in response to an image of the one or more fiducials.

Clause 56. A method of using fiducials with a drape comprising: coupling a probe comprising an elongate shaft and an elongate axis to an arm; covering the probe with a drape; and coupling a fiducial assembly to the probe across the drape, the drape between the fiducial assembly and the probe, the fiducial assembly comprising: a base; a coupling attached to the base and configured to couple the fiducial assembly to the probe across the drape; and one or more fiducials attached to the base.

Clause 57. The method of clause 56, further comprising: moving the surgical probe beneath the surgical drape based on an orientation of the probe determined from the fiducials.

Clause 58. The method of clause 56, wherein the fiducials comprise light sources.

Clause 59. The method of clause 56, wherein the fiducials comprise light reflectors.

Clause 60. The method of clause 56, wherein the one or more fiducials comprise a single two-dimensional fiducial.

Clause 61. The method of clause 56, wherein the fiducial is coupled on a first side of the surgical drape at least a portion of the surgical probe is located on a second side of the surgical drape.

Clause 62. The method of clause 56, wherein the probe comprises one or more of an imaging probe or a treatment probe.

Clause 63. The method of clause 56, wherein the coupling comprises magnetic couplings.

Clause 64. The method of any one of clauses 56-63, wherein the couplings are configured to couple the fiducial assembly to the surgical probe in a single orientation.

Clause 65. The method of clause 56, wherein the couplings couple the surgical drape, the surgical probe, and the fiducial assembly together.

Clause 66. A method of using a drape comprising: covering a non-sterile instrument driver with a drape; coupling a sterile probe to the instrument driver, with the surgical drape therebetween, wherein one or more sterile fiducials is coupled to the sterile probe in a fixed special relationship with the sterile portion of the surgical probe.

Clause 67. The method of clause 66, further comprising: inserting a portion of the non-sterile portion of the surgical probe through a fenestration in the surgical drape.

Clause 68. The method of clause 67, further comprising: capturing a perimeter of the fenestration between the sterile portion and the non-sterile portion of the surgical drape.

Clause 69. The method of clause 68, further comprising: moving the surgical probe beneath the surgical drape based on an orientation of the probe determined from the one or more fiducials.

Clause 70. The method of clause 66, wherein the one or more fiducials is configured to be located on a sterile side of the surgical drape.

Clause 71. The method of clause 66, wherein the one or more fiducials is configured to be located on a first side of the surgical drape and at least a portion of the surgical probe is configured to be located on a second side of the surgical drape.

Clause 72. The method of clause 66, wherein the one or more fiducials is integral with the sterile portion.

Clause 73. The method of clause 66, wherein the one or more fiducials extends directly form the sterile portion.

Clause 74. The method of clause 73, wherein the one or more fiducials includes three fiducials defining a plane.

Clause 75. The method of clause 66, wherein the one or more fiducials is integrated into the sterile portion.

Clause 76. The system or method of any one of the preceding clauses, wherein the one or more cameras comprises a stereo camera.

Clause 77. The system or method of any one of the preceding clauses wherein the one or more cameras comprises a plurality of cameras.

Clause 78. The system or method of any one of the preceding clauses wherein the one or more cameras comprises a single camera.

Clause 79. The system or method of any one of the preceding clauses wherein a processor is configured to output an indication to a user to adjust the probe in response to one or more of the position or the orientation of the probe.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A fiducial system for use with a drape comprising:
   a fiducial assembly configured to couple to a probe across the drape with a fixed orientation and offset relative to an elongate axis of the probe, the fiducial assembly comprising:
   a base;
   a coupling attached to the base and configured to couple the fiducial assembly to the probe across the drape, wherein a first portion of the coupling is located on the probe and a second portion of the coupling is located on the fiducial assembly, the first portion configured to couple to the second portion with the drape between the first portion and the second portion; and
   one or more fiducials attached to the base.

2. The fiducial system of claim 1, wherein the one or more fiducials comprises a two-dimensional fiducial.

3. The fiducial system of claim 2, wherein the one or more fiducials comprises a two-dimensional fiducial array.

4. The fiducial system of claim 2, wherein two dimensional fiducial comprise a first fiducial, a second fiducial, and a third fiducial arranged along a plane.

5. The fiducial system of claim 1, wherein the fiducial assembly further comprises:
   a fiducial tree extending from the base, the one or more fiducials attached to branches of the fiducial tree.

6. The fiducial system of claim 1, wherein the one or more fiducials comprise light sources.

7. The fiducial system of claim 1, wherein the one or more fiducials comprise light reflectors.

8. The fiducial system of claim 1, wherein the one or more fiducials comprise a single two-dimensional fiducial.

9. The fiducial system of claim 1, wherein the probe comprises one or more of an imaging probe or a treatment probe.

10. The fiducial system of claim 1, wherein the one or more fiducials is configured to be located on a sterile side of the drape and at least portion of the probe is configured to be located on a non-sterile side of the drape.

11. The fiducial system of claim 1, wherein the one or more fiducials is configured to be located on a first side of the drape at least a portion of the probe is configured to be located on a second side of the drape.

12. The fiducial system of claim 1, wherein the coupling couples the drape, the probe, and the fiducial assembly together.

13. The fiducial system of claim 1, wherein the coupling comprises magnetic couplings.

14. The fiducial system of claim 1, wherein the coupling comprises a snap coupling.

15. The fiducial system of claim 1, wherein the coupling comprises a stud portion located one of the probe or the fiducial assembly and the second portion including a socket located on a second one of the probe or the fiducial assembly.

16. The fiducial system of claim 1, wherein the coupling is configured to couple the fiducial assembly to the probe in a single orientation.

17. The fiducial system of claim 16, wherein the coupling is configured to couple the fiducial assembly to the probe at a single position and the single orientation with respect to the probe.

18. The fiducial system of claim 17, wherein the coupling and the one or more fiducials are configured to couple the one or more fiducials to the probe with a fixed offset distance from the elongate axis and a fixed location along the elongate axis.

19. The fiducial system of claim 18, wherein the fixed location along the elongate axis corresponds to a fixed distance between the fixed location and a distal tip of the probe.

* * * * *